(12) United States Patent
Wynne

(10) Patent No.: US 7,396,590 B2
(45) Date of Patent: Jul. 8, 2008

(54) SOFT BLOCK WITH REPEAT UNITS THAT FAVOR MIGRATION TO A SURFACE AND REPEAT UNITS WITH AN ACTIVITY OF INTEREST, AND POLYMERIC ARTICLES OR COATINGS USING SAME

(75) Inventor: Kenneth Joseph Wynne, Richmond, VA (US)

(73) Assignee: Virginia Commonwealth University, Richmond, VA (US)

( * ) Notice: Subject to any disclaimer, the term of this patent is extended or adjusted under 35 U.S.C. 154(b) by 49 days.

(21) Appl. No.: 10/882,238

(22) Filed: Jul. 2, 2004

(65) Prior Publication Data

US 2005/0084683 A1    Apr. 21, 2005

Related U.S. Application Data

(60) Provisional application No. 60/485,494, filed on Jul. 9, 2003.

(51) Int. Cl.
  *B32B 27/04* (2006.01)
  *B32B 27/28* (2006.01)
  *B32B 27/40* (2006.01)
(52) U.S. Cl. .................................. 428/421; 428/423.1
(58) Field of Classification Search ............ 428/423.1, 428/421; 548/333.5
See application file for complete search history.

(56) References Cited

U.S. PATENT DOCUMENTS

| | | | |
|---|---|---|---|
| 5,637,772 A | | 6/1997 | Malik et al. |
| 5,807,977 A | | 9/1998 | Malik et al. |
| 6,037,483 A | | 3/2000 | Malik et al. |
| 6,127,507 A | * | 10/2000 | Santerre ............... 528/66 |
| 6,469,177 B1 | | 10/2002 | Worley et al. |
| 6,479,623 B1 | | 11/2002 | Malik et al. |

FOREIGN PATENT DOCUMENTS

WO    WO 02/057340    7/2002

* cited by examiner

*Primary Examiner*—Thao Tran
(74) *Attorney, Agent, or Firm*—Whitham Curtis Christofferson & Cook, P.C.

(57) ABSTRACT

Polymers, and particularly conventional commodity bulk polymers, are modified to have a surface activity of interest using a surface modifying polymer that includes a moiety that favors migration to the surface of the bulk polymer together with a moiety provides the activity of interest (e.g., biocidal, wettability modifying (hydrophobic or hydrophilic), resistance to radiant energy, providing a functional group for functionalizing the surface, etc.). The surface modifying polymer is combined with the bulk polymer, and, due to the presence of the moiety that favors migration, concentrates primarily on the surface of the bulk polymer such that the moiety that provides the activity of interest is located primarily on the surface of the bulk polymeric article which is produced.

17 Claims, 9 Drawing Sheets

Biocidal Evaluation: Modified AATCC-100 test

Bacterial Challenge: *E. coli*

PU Control
> 400 cfu's

98% PU, 2% Biocidal SMA
0 cfu's

Result: Modified AATCC-100 test
- Coating: 98% PU, 2% Biocidal SMA
- Killed all bacteria present (30 min)
- Minimum of 99.9% or 3.6 log reduction

SOFT BLOCK WITH REPEAT UNITS THAT FAVOR MIGRATION TO A SURFACE AND REPEAT UNITS WITH AN ACTIVITY OF INTEREST, AND POLYMERIC ARTICLES OR COATINGS USING SAME

CROSS-REFERENCE TO RELATED APPLICATIONS

This patent application is related to U.S. Provisional Application 60/485,494 filed Jul. 9, 2003, and the complete contents of that application is herein incorporated by reference.

This invention was made using grants from the U.S. Government, particularly NSF (523279), DARPA (528979), and the government may have certain rights under the patent.

BACKGROUND OF THE INVENTION

1. Field of the Invention

The present invention generally relates to a method for modifying the surface of conventional commodity polymers, including without limitation polyurethanes, polyesters, polyethers, polyamides, polyimides, etc.

2. Background Description

Surface modification of a polymeric article is performed or attempted for a number of different reasons. For example, it may be desirable to have a bulk polymer that has a surface that is modified to better accept a paint or dye, or to have a surface that imparts a property such as resistance to chemical or radiant energy damage.

A number of different methods have been developed for modifying the surfaces of a polymer. Many of these methods involve post processing of the article. For example, the polymeric article may be exposed to a plasma, or a plasma processing step followed by grafting of compounds to the surface of the polymer. Also, the polymeric article might be subjected to a chemical or radiant energy exposure to alter the surface. It is known to combine a fluorinated polymer with a conventional polymer to get the surface-concentrated fluoropolymer. (Ji, Q.; Kang, H.; Wang, J.; Wang, S.; Glass, T. E.; McGrath, J. E., Surface characterization of fluorinated oxetane polyol modified polyurethane block copolymers, *Polymer Preprints*, 2000, 41, 346-347.) It is known that combining a fluorinated group with a UV absorbing chromophore surface-concentrates the chromophore.(Vogl, O.; Jaycox, G. D.; Hatada, K., Macromolecular design and architecture, *Journal of Macromolecular Science-Chemistry*, 1990, 27, 1781-1854.) It is known that combining a perfluorohexyl group with a fullerene surface-concentrates the fullerene at a styrene air interface. (Chen, W.; McCarthy, T. J., Adsorption/migration of a perfluorohexylated fullerene from the bulk to the polymer/air interface, *Macromolecules*, 1999, 32, 2342-2347.)

SUMMARY OF THE INVENTION

It is therefore an object of the invention to provide polymeric articles or coatings, and methods of making polymeric articles or coatings, where the polymeric article has a surface phase having an activity of interest.

According to the invention, there is provided a methodology for preparing polymer articles or coatings which have a surface phase with an activity of interest. It is understood that a telechelic is an oligomeric or polymeric material with reactive groups usually at the chain ends and may also be called a macromonomer. In the methodology, a surface active telechelic or polymer is prepared which includes both a surface active segmer which favors migration to the surface of a bulk polymer and one or more functional segmers which provide an activity of interest (e.g., biocide, bioactive, UV protective, hydrophobic, hydrophilic, etc.). When combined with bulk polymer, the surface active segmers bring the functional segmers to the surface of the polymeric article during processing (e.g., creation of a coating, extruding, etc.). In one embodiment, the surface modifying additive are one or more telechelics that contain fluorinated surface-active segmers and functional segmers or one or more polyurethanes comprised of conventional hard block forming units (diisocyanates and diols and/or diamines) and soft blocks that contain fluorinated surface-active segmers and functional segmers. The surface-active segmers bring the functional segmers to the surface and together these segmers constitute the functional surface-active soft block of the surface modifiers (SMs). To demonstrate a specific embodiment in a broad range of possible functional SMs, biocidal SMs have been prepared by preparing polyurethane SMs comprised of isophorone diisocyananate/butane diol hard blocks and soft blocks comprised of fluorinated segmers (surface active) combined with biocidal moieties (function) in soft blocks. After activation, these SMs effectively kill pathogen challenges on contact demonstrating the efficacy of the SM concept. Additional examples demonstrate that SMs confer unusual wetting behavior on the substrate polymer. Such tailored change may find use in biomaterials, filters, cosmetics, and other areas where surface properties such as feel and capability to attract moisture are important. It is understood in the context of this patent, that the terms telechelic and macromonomer are used interchangeably. Furthermore, it is understood that when a statement is made such as "telechelic in the polyurethane" that the terminal reactive groups present on the telechelic are no longer present but changed to appropriate functionality by virtue of incorporation (e.g, a urethane group if reaction occurs between an alcohol group on the telechelic with an isocyanate on the hard block).

BRIEF DESCRIPTION OF THE DRAWINGS

The foregoing and other objects, aspects and advantages will be better understood from the following detailed description of a preferred embodiment of the invention with reference to the drawings, in which.

DETAILED DESCRIPTION OF A PREFERRED EMBODIMENT OF THE INVENTION

Figure 1:
FIG. 1 is a schematic generalized representation of a surface active modifier and bulk substrate.

The general concept of a surface modification contemplated by the present invention is shown in FIG. 1. The objective is to modify the surface of a coating or molded object, referred to generically as a polymeric article 10 to include a surface domain 12 which has a property of interest without affecting the bulk properties in the bulk domain 14.

The invention generally relates to polymeric additives that act to modify the surface properties of conventional commodity polymers. This is achieved by synthesis of polymeric surface modifiers (SMs), sometimes referred to as surface modifier additives (SMAs) with a structure that favors migration to the surface of a bulk polymer. In particular, the surface-philic character of the SMs depends on the presence of a functional block, which is preferably a "soft block" or flexible chain segment that contains a surface-active segmer and a functional segmer. The approach leverages the general tendency of soft blocks to surface segregate, the presence of surface active groups such as fluorinated groups (inclusive of fully fluorinated or semifluorinated groups [e.g., —(CH$_2$)n(CF$_2$)mF, —(CH$_2$)n(CF$_2$)mH] where n is typically 1-10 and m is typically 1-12] in the soft segment, and the synergistic combination of surface-philic soft blocks with a multiplicity of surface active groups.

Figure 2:
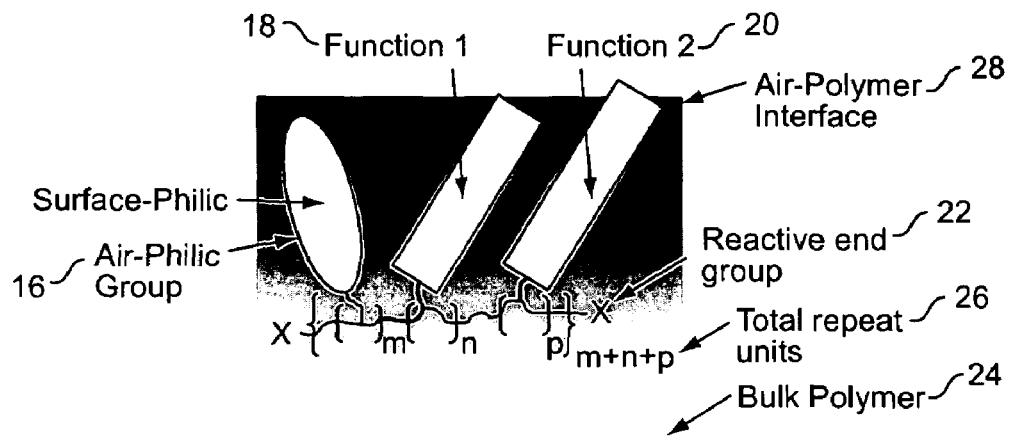
FIG. 2 is a schematic representation of a surface active functional soft block.
Figure 4:
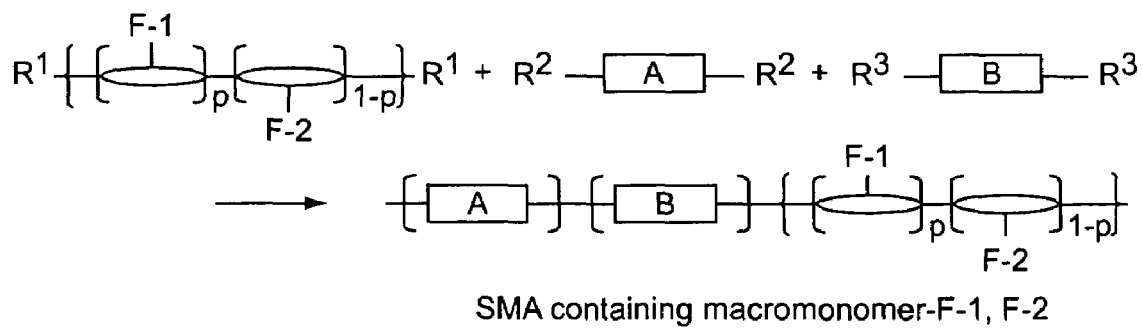
FIG. 4 is a schematic flow diagram representation showing the incorporation of the macromonomer of FIG. 3 into a polymer to form a surface modifying additive (SMA) polymer which contains the macromonomer.

A general structure for such a soft block is shown in FIG. 2. The exact embodiment will depend on the commodity or bulk polymer chosen for modification. In particular, an air philic group 16, such as a semifluorinated group, is combined in the soft block with one or more functional moieties 18 and 20 shown for exemplary purposes as function 1 and function 2, respectively. The telechelic may have reactive end groups 22 which may polymerize with monomers for the purpose of incorporation into an SMA as shown in FIG. 4. The telechelic block is itself preferably a polymer where the number of repeat units 26 m+n+p is preferably more than one for each unit, and most preferably ranging between 2 and 200 for each unit. The functional soft block may be used alone or incorporated in a segmented copolymer to effect the preparation of a new kind of SM. The SM is added to a commodity polymer or "base" polymer that has desired bulk properties. The resulting blend is represented schematically in FIG. 1. The SM determines the surface properties by virtue of concentration of the SM at the surface, or air-polymer interface 28 as shown in FIG. 2, during ordinary processing conditions such as coating or extrusion.

There are two general ways that an SM may be employed. One is literally as an additive. That is, the SM is added to some substrate system such as a liquid or solid coating composition. A second way is to spray or coat an extremely thin film on an already formed object such as a filter (e.g., the SM alone or with the bulk polymer are sprayed or coated onto the surface of a filter with the SM migrating to the surface of the coating). In either case, the combination of properties provided by the soft block structure illustrated in FIG. 2 will assure that the function of interest will be surface concentrated.

The SM of this invention is generated in different ways. One method starts with the synthesis of monomers with suitable functions, the polymerization of monomers to co-macromonomers (co-telechelics), and the generation of an SM by incorporating the co-macromonomers into a polymer. A second method involves the modification of an SM polymer to generate the desired functional SM.

Figure 3:
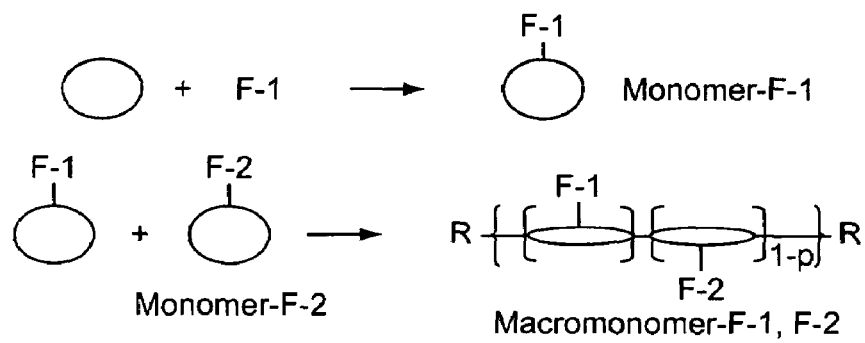
FIG. 3 is a schematic flow diagram showing monomer modification by introducing functional groups, and copolymerizing to form a telechelic.

With reference to FIGS. 3 and 4, the circle represents a cyclic monomer substrate; R or R$^1$ preferably represents a reactive functional group introduced in ring opening polymerization such as the hydroxy group —OH or amino group —NH$_2$; P is the mole fraction of monomer containing function F1; A and B are polymer forming moieties such as isocyanates and alcohol terminated chain extenders (reactive groups R$^2$ and R$^3$), respectively, for polyurethane formation for example, isocyanates and amine terminated chain extenders for polyurethane urea formation for example, or only monomer or polymer "A" might be needed (e.g., a dicarboxylic acid) for ester formation, for example.

With reference to FIG. 3, the SM may be generated by synthesizing monomers F1 and F2 (F2 may itself be synthesized by similar procedures used for F1), and then copolymerizing the monomers. This creates a macromonomer having F1 and F2 functions, and the macromonomer itself may be a soft block or polymer. In a preferred embodiment, the macromonomer is incorporated into (e.g., polymerized with or grafted on, etc.) another polymer at either or both of its end groups R to form the desired SM. See, for example, the creation of a copolymer with monomers A and B and the macromonomer containing F1 and F2 in FIG. 4. In the present invention, either F1 or F2 must be a segmer which preferentially migrates to the surface of a polymer during casting, extrusion, coating, etc. Once formed, the macromonomer (FIG. 3) and/or polymer containing the macromonomer (FIG. 4) which separately or together are the surface modifiers (SM) is mixed (typically 2% by weight or less) into a desired base polymer to give a solid with a modified surface as shown in FIG. 1.

Figure 5:
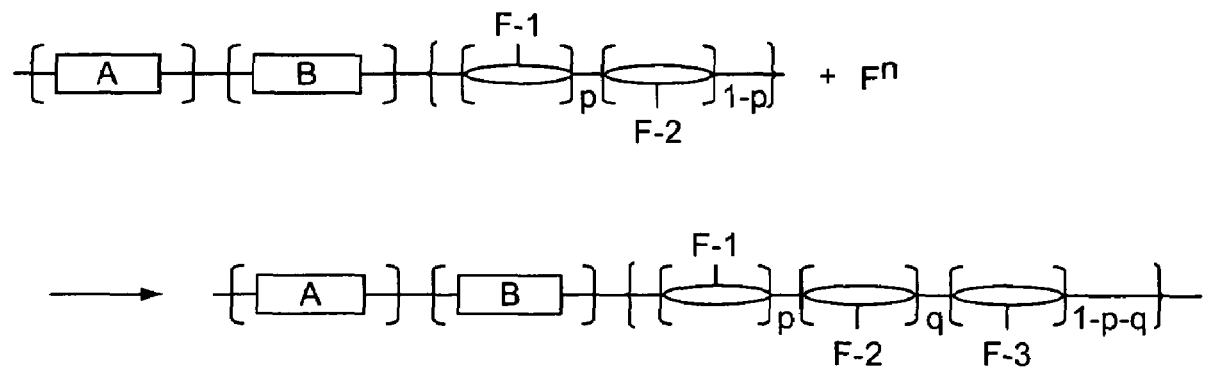
FIG. 5 is a schematic flow diagram showing the subsequent modification of the SMA of FIG. 4 to introduce a desired functionality.

FIG. 5 shows an existing SM containing macromonomer (e.g., a polymer containing A, B, and soft block containing F1 and F2) being modified to include a desired functionality F3. Here, a desired functionality F3 is introduced by reaction of an existing SM with Fn to give a new SM polymer. Supposing that Fn reacts with F2 to give F3, the reaction may be complete, in which case q is zero. However, if Fn reacts with F2 to give F3, the reaction may be incomplete, in which case q is finite and the macromonomer (SM polymer) contains three functional repeat units F1, F2, and F3. Examples of Fn include pre-biocidal moieties such as 5,5-dimethylhydantoin, hydrophilic groups such as polyethylene oxide moieties (e.g., $CH_3O(CH_2CH_2O)n$-, where n=0-15), alcohols (such as —$CH_2$)nOH), or where n=1-10); and/or amines, such as —$(CH_2)nNH_2$, where n=1-10), chromophoric groups, alkylammonium groups (that may have biocidal character) such as (—$NH_2(CH_2)nH)^+$, where n=1-20, and combinations ("libraries") of these groups to generate surfaces with specialized properties such as wetting behavior, response to acidic and/or basic conditions or selective detection of target molecules, and/or biocidal activity.

Another example of Fn is a group that has protected functionality such as a —$Si(OR)_3$ group (R=—$(CH_2)nH$, where n=1-5, and includes Me, Et, isopropyl, propyl, etc., acetato, and other hydrolysable groups). By "protected" is meant that upon exposure to a suitable reagent, a chemical change takes place that produces a new kind of functionality. In the case of —$Si(OR)_3$, exposure to moist air or mild acid produces the —$Si(OH)_3$ group which is hydrophilic and can undergo a crosslinking reaction to produce a siliceous domain by well known condensation reactions releasing water. This importance of this approach is that a —$Si(OH)_3$ group would normally not migrate to the air polymer interface as it is a high energy group that prefers to remain in the bulk.

The functional group F2 (or F3) could be a trimethylsilyl or similar group such as an oligosiloxane (—$(CH_2)n[Si(Me_2)O]mSiMe_3$). This cotelechelic may have some unusual combination of hydrophobic/oleophobic behavior as surface active groups such as semifluorinated groups (F1) are oleophobic and hydrophobic, but groups such as trimethylsilyl (or oligosiloxane) are only hydrophobic (but not oleophobic).

In testing the new approach to surface functionalization contemplated by this invention, the C—Br group has been introduced as a model functionality, and is described in detail in Example 1. Another group of macromonomers containing $CH_3O(CH_2CH_2O)n$-has been prepared to test the surface modified additive approach of the present invention, and is described in detail in Examples 2 and 3. Examples 1, 2 and 3 fall into class I described by FIG. 3 (co-monomers→cotelechelic→polyurethane SMA with cotelechelic-derived soft block). Examples 4 and 5 describe a "reaction on polymer" approach as described in FIG. 5.

Figure 6:
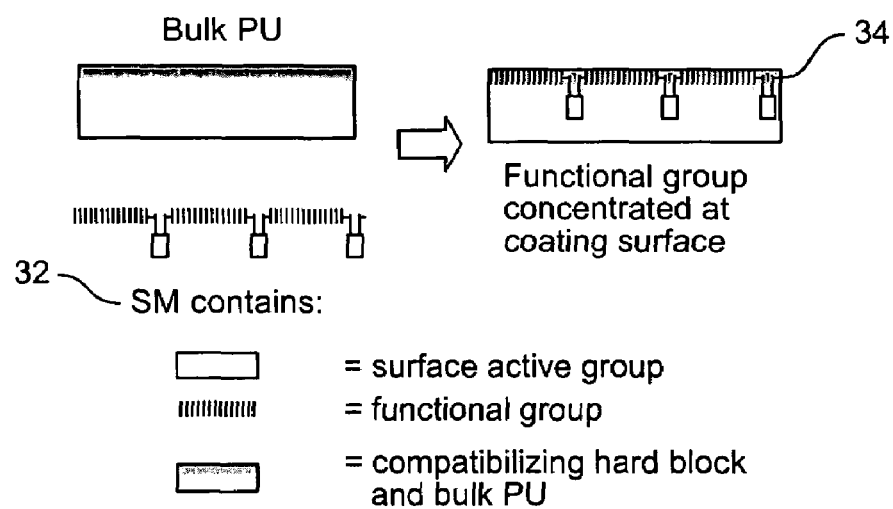
FIG. 6 is a schematic representation of a polyurethane surface modifier.

In one embodiment, the SMs can be polyurethanes. Polyurethanes (PU) are used in a variety of applications, and are an excellent model for the general application of the present invention because of their broad use and robust character. The general scheme for polyurethane surface modifiers is shown in FIG. 6, where a bulk polyurethane 30 is combined with a surface modifier 32 which contains an active group, a functional group, and a compatibilizing hard block to yield a product 34 with a functional group concentrated at the coating surface. In this specific embodiment of the general concept, surface active and functional groups are incorporated into the soft block. This approach takes advantage of both surface concentration of soft blocks and surface-philicity of fluorinated groups. Further details are provided in Examples 4 and 5.

Figure 7:
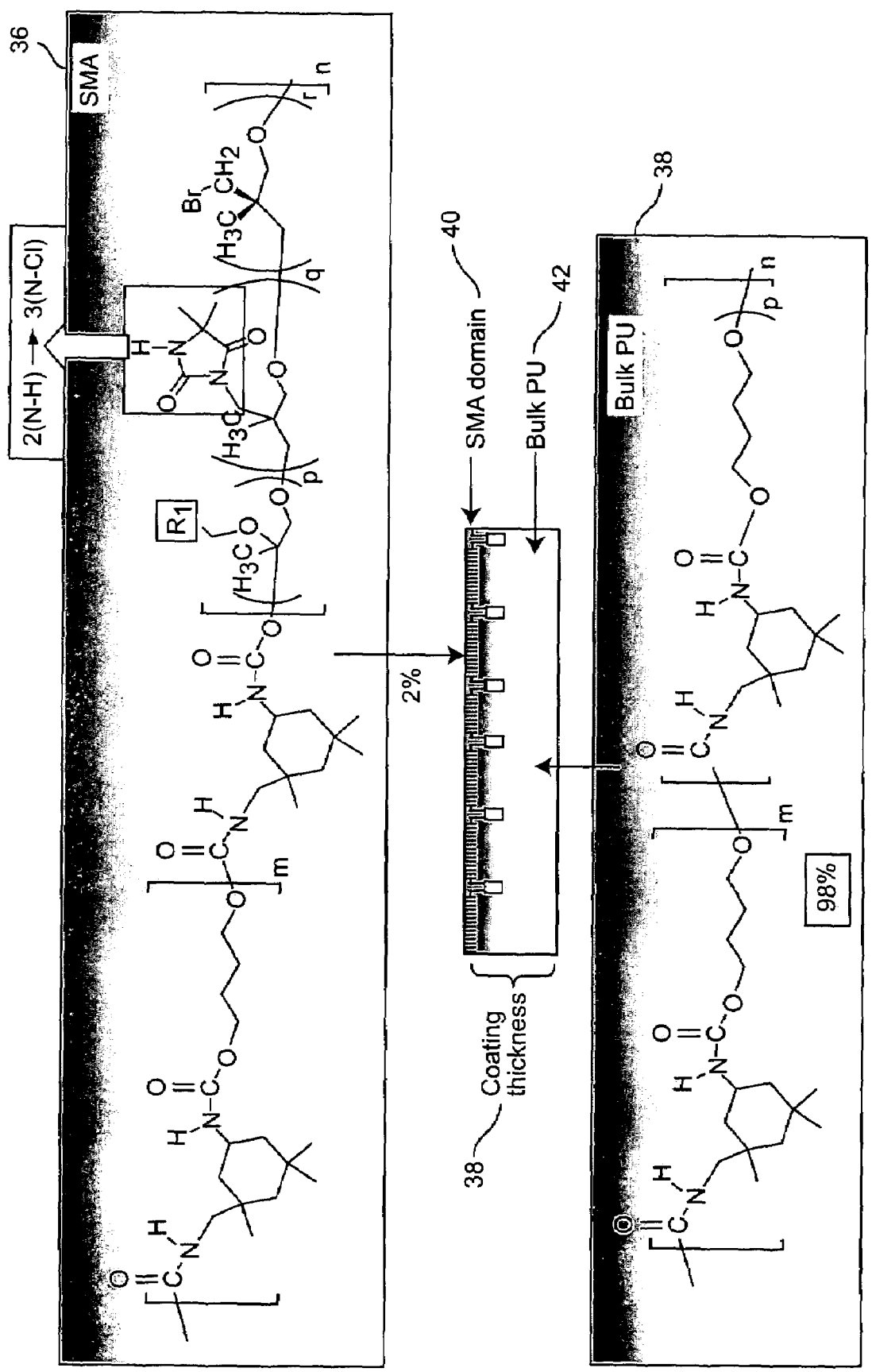
FIG. 7 is a schematic diagram showing surface functionalization via the inventive SMA approach illustrated by the addition of 2% gen-1-SMA (PU-SMA 2) to and IPDI/BD/PTMO polyurethane (PU-1), where the conversion of near surface amide to a chlorimide SMA-Cl, is highlighted in a box at the top.

The specific functionality incorporated in the soft block in Example 1 is a reactive —C—Br group. In Examples 2 and 3, a hydrophilic ethylene oxide moiety is introduced. In Example 4, a hydantoin, 5,5-dimethylhydantoin is introduced, which confers on the surface of the SMA itself unusual wetting behavior. In Example 5, the surface-concentrated pre-biocide depicted in FIG. 7 is reacted with bleach to generate surface concentrated, biocidal chloramide function. However, it should be understood that a wide variety of functionalities (that is groups other than the F3 (FIG. 5) prebiocidal hydantoin group) could be used in the practice of this invention including without limitation the groups noted above.

In order to obtain surface-active telechelics bearing reactive groups, co-telechelics containing semifluorinated and bromomethyl groups can be prepared. 3-bromomethyl-3-methyloxetane (BrOx) is readily available and offers a reactive group for subsequent derivitization. Homo- and co-polymerization of BrOx with 3FOx (—$CH_2CF_3$) and 5FOx (—$CH_2CF_2CF_3$) is contemplated in this exemplary process. Using the FOx/BrOx telechelics, polyurethanes were prepared employing isophorone diisocyanate (IPDI)/butane diol (BD) hard blocks. Most work was done using a 40% hard block polyurethane IPDI-BD(40%)-3FOx/BrOx(1:1), where 40% is percent hard block and 1:1 signifies the mole ratio of 3FOx to BrOx. Example 1 provides details.

As described in Example 5, the pre-biocidal functional group 5,5-dimethylhydantoin (Hy) was introduced into by a "reaction on polymer" carried out in dimethyl formamide (DMF). FIG. 7 shows the resulting SMA 36 as IPDI-BD-(3FOx/BrOx/HyOx)(1:0.3:0.7) where HyOx is a substituted oxetane segmer containing the hydantoin moiety. This was combined with bulk polyurethane 38 (conventional IPDI-BD-PTMO-2000 (40% hard block) polyurethane) at 2 wt % SMA 36, 98 wt % bulk polyurethane 38 mixture. The coating 38 thus formed included an SMA domain 40, and a bulk polyurethane domain 42. Evidence for the surface concentration of 2% SMA-98% polyurethane came from Wilhelmy plate analysis and biocidal activity.

It will be understood that the concentration of the SMA in the polymeric article or coating to be formed can vary depending on the application. It will typically constitute 10% or less by weight, and most preferably 0.1-3 weight percent of the polymeric article or coating. Even lower percentages may be adequate depending on the application and the SM composition and processes. Some SMs are more efficient surface concentrators than others.

As will be discussed below, this invention can be employed to make a biocidal SMA such that a polymeric article or coating formed according to the invention has an underlying bulk polymer domain and a surface domain having a SMA with biocidal activity. This might, for example, be especially useful in the hospital or clinic setting wherein gloves, countertops, examining tables, surgical equipment and tools, wall paper, surfaces of computer keyboards, cellphones and pagers, and cabinetry can have polymer coating that provides a biocidal activity. The biocidal activity may also be useful in other settings such as schools and offices where large numbers of people are gathered. The biocidal activity may be useful in modifying air filters, by, for example, applying a microcoating on the filter material or creating the filter from the SMA and bulk polymer mixture, so as to not only trap pathogens or agents but to inactivate them.

It should be understood that the invention can be used to impart a surface domain to a bulk polymer where the surface domain has a variety of other desired activities. For example, in automobile applications it may be desirable to apply a polymer coating where the surface domain repels water or corrosive agents. This would require forming an SMA with functional group segmers that make the surface of the polymer coating more repellant to water (e.g., combining both fluorinated groups (F1) with trimethylsilylated (or oligosiloxane) groups (F2) as noted above might be used. Conversely, in paper or sign making applications where it is desirable to accept dyes, colorants, paints, or the like, the SMA would be formed with functional group segmers that make the polymer coating more hydrophilic (e.g., hydrophilic groups such as polyethylene oxide moieties (e.g., $CH_3O(CH_2CH_2O)n$-, where n=0-15), alcohols (such as —$(CH_2)nOH$), or where n=1-10); and/or amines, such as —$(CH_2)nNH_2$, where n=1-10) and their derived ammonium salts (as —$(CH_2)nNH_3^+$, where n=1-10), chromophoric groups, alkylammonium groups such as (—$NH_2(CH_2)nH)^+$, where n=1-20, and combinations ("libraries") of these groups to generate surfaces with specialized wetting behavior properties.

As another example, it may be desirable to provide a means for functionalizing the surface of the polymer with leaving groups (e.g., Br) such that the surface could be derivitized with compounds of interest. In this instance, the invention may allow the formation of diagnostic chips that have DNA, RNA, amino acids, amino acid sequences, or other biological materials of interest bonded to the surface of a polymer coating by way of interaction with the functional leaving group.

As yet another example, the surface of a polymer can include a functional segmer which enables a fluorescent, phosphorescent, chemiluminescent, or color change reaction to occur when the functional segmer is in contact with a particular agent. This property would find sensing/detection utility in diagnostic devices, as well as in applications such as signs and displays. In still another application of the invention, fiber optics can be extruded where the surface of the optic includes the surface-active agent, which thus encircles the core. For example, in the fiber optic application, the surface modifier might prevent UV or other radiant energy from transmission to the core or, by virtue of interaction with the evanescent surface wave might act as an optical sensor/detector.

In the exemplary case of a biocidal SMA [FIG. 7, Example 5], the SMA was prepared via the method shown in FIG. 5, wherein "A" and "B" together represent a hard block in a polyurethane (PU) derived from isophorone diisocyanate (A) and butane diol (B). The low Tg block is a copolymer where F1 is a fluorinated group (3-FOx) and F2 is a bromomethyl group. In this case, not all the bromomethyl groups are replaced by biocide precursor 5,5-dimethylhydantoin (F3) so that the resulting SMA has three repeat units (F1, the fluorinated group, F2, the unreplaced bromomethyl groups, and F3, the pre-biocidal moiety 5,5-dimethylhydantoin). The resulting SMA has been added to a base polyurethane, treated with bleach to generate the biocidal N—Cl group (N-halamine) and tested against several pathogens. N-halamines are discussed in detail in U.S. Pat. No. 6,469,177 to Worley, which is herein incorporated by reference. As discussed in detail in Example 5, in 30 min exposure, 99.999% or >5.2 log reduction of *Pseudomonas aeruginosa* was observed against a suitable control. This sets a minimum for biocidal activity as no surviving bacteria were found after exposure to the SMA modified PU. Similar results were obtained for *Staphylococcus aureus* and *E. coli*.

The synthesis and characterization of nonionic detergents is well known. Such molecules have an amphiphilic structure. That is, one end of the molecule may be hydrophilic, while the other end is oleophilic. Molecules that have one hydrocarbon end one poly(ethylene oxide) end are examples. The bifunctional telechelics described herein may find use as polymeric nonionic detergents. For example, the block telechelics described in Example 2 have a fluorocarbon end (hydrophobic, oleophobic) and an oligomeric ethylene oxide end (hydrophilic). Such architecture is uncommon. This architecture would mediate between fluorocarbon-like and water-like phases. For example, such a detergent might be useful in emulsifying materials that are insoluble in water, supercritical $CO_2$, or other solvent. Such a structure could prevent phase separation between immiscible polymers.

Even the random copolymer may be useful as a nonionic detergent because of the extreme difference solubility parameter between fluorinated substituents (that can be widely varied) and hydrophilic side chains (that can also be widely varied). This application would be novel for all binary and ternary combinations of:

Oleophilic groups such as (—$CH_2$)nH, tetramethylene oxide, isomeric hydrocarbon and hydrocarbon-halocarbon (—CHxCl)H, ketone containing, side chains Hydrophilic groups such as aforementioned oligomeric and polymeric ethylene oxide, alcohol, carboxylic acid, amine containing side chains Fluorous groups such as those aforementioned [e.g., —$(CH_2)n(CF_2)mF$, —$(CH_2)n(CF_2)mH$) where n is typically 1-10 and m is typically 1-12]

In view of the contemplation of use of molten salts as reaction media and other applications for amphiphilic (and even triphilic) molecules, molecules with cationic (typically alkyl ammonium) or anionic (typically carboxylate, sulfate, sulfonate, phophonate) functionality are readily envisaged and could be used in combination with oleophilic, hydrophilic, and fluorous groups described above.

EXAMPLE 1

Homo- and copolymerization of BrOx and FOx monomers were carried out by a modification of the procedure reported by Malik. [Malik, A. A.; Archibald, T. G.; GenCorp: US, 2000.] Cationic ring opening polymerization was employed with $BF_3$ dietherate and 1,4-butanediol as catalyst and co-catalyst, respectively, to give the desired telechelic. A typical procedure follows.

Copolymerization of 3-trifluoroethoxy-3-methyloxetane (3FOx) and 3-bromomethyl-3-methyloxetane (BrOx) monomers were carried out by a modification of a published procedure. Cationic ring opening polymerization was employed using $BF_3OEt_2$ and 1,4-butanediol as catalyst and co-catalyst, respectively. Methylene chloride (5.54 ml) was poured into a round bottom flask under nitrogen. 1,4-butanediol (0.77 g, 8.54 mmol) and $BF_3$-$OEt_2$ (2.45 g, 17.27 mmol) were added into reaction medium and stirred at room temperature for 45 min under nitrogen purge. Then the solution was cooled to −20° C. by using dry/aqueous isopropyl alcohol mixture. Mixture of 3FOx and BrOx monomers (e.g., total 30.09 g, 172.43 mmol) in methylene chloride (42.10 ml) was added drop wise with an addition rate of 170 drops/min. The reaction temperature was kept at −25 to −30° C. by addition of extra dry ice for 5 hrs. The reaction mixture was then brought to room temperature and quenched with 50 ml of water. The organic phase was separated, washed with 2 wt % aqueous HCl and NaCl solutions and then precipitated into methanol/water mixture (5:1). The precipitated macromonomer was placed into vacuum oven for overnight drying at 50° C., 4 Torr. The product was viscous, slightly opaque with more than 85% yield.

A number of FOx-BrOx telechelics were made by a similar procedure. The compositions and molecular weights are shown in Table 1 below:

TABLE 1

Compositions and molecular weights of telechelic poly(oxetanes).

| Telechelic | Monomer feed ratio[a,b] | | | Poly(oxetane) telechelics | | |
|---|---|---|---|---|---|---|
| | 3FOx | 5FOx | BrOx | FOx:BrOx[c] | $D_p$[c] | MW[c,d,e] |
| 3FOx | 1.0 | — | — | — | 18.5 | 3400 |
| 5FOx | — | 1.0 | — | — | 24.2 | 5660 |
| BrOx | — | — | 1.0 | — | 17.1 | 2820 |
| 3FOx:BrOx-1:1 | 1.0 | — | 1.0 | 1.2:1.0 | 27.0 | 4710 |
| 3FOx:BrOx-2:1 | 2.0 | — | 1.0 | 2.2:1.0 | 26.5 | 4700 |
| 3FOx:BrOx-1:2 | 1.0 | — | 2.0 | 1.0:1.7 | 19.6 | 3360 |
| 5FOx:BrOx-1:1 | — | 1.0 | 1.0 | 1.2:1.0 | 20.5 | 4085 |
| 5FOx:BrOx-2:1 | — | 2.0 | 1.0 | 1.9:1.0 | 11.9 | 2500 |
| 5FOx:BrOx-1:2 | — | 1.0 | 2.0 | 1.0:1.8 | 18.1 | 3400 |

[a]Monomer/catalyst ($BF_3$—$OEt_2$) mole ratio = 10.
[b]Catalyst ($BF_3$—$OEt_2$)/cocatalyst (1,4-butanediol) mole ratio = 2.02.
[c]Determined by $^1$H-NMR end group analysis.
[d]$M_w$ by GPC with PS standards (universal calibration): BrOx; 2600, 5FOx:BrOx-1:2; 5800, 3FOx:BrOx-1:2; 4100
[e]Polydispersities for these three telechelics by GPC were: BrOx 1.58, 5FOx:BrOx-1:2; 1.35, 3FOx:BrOx-1:2; 2.04.

Table 1 lists telechelic molecular weights determined by end group analysis. Molecular weights were obtained by integrating the high field methylene peaks next to the trifluoroacetyl group at 4.2-4.3 ppm and methyl peaks in FOx at 0.92 ppm(CH3, FOx) and BrOx at 1.05 ppm (CH3, BrOx). In previous reports, homotelechelic molecular weights were determined by integrating the low field methyl peaks (due to terminal residues) and the main chain ones [Malik, A. A.; Carlson, R. P. U.S. Pat. No. 5,637,772, 1997, which is herein incorporated by reference]. Molecular weights were determined by GPC (in THF compared to PS standards) for those telechelics not having a refractive index matching THF. The observed values for Mw and Mn (footnote to Table 1) values give the following polydispersities: 1.58 for BrOx, 2.04 for 3FOx:BrOx-1:2, and 1.35 for 5FOx:BrOx-1:2. These values are similar to those previously reported for 3FOx and 5FOx polyoxetane telechelics polymerized using the BF3 THF/ neopentyl glycol catalyst/co-catalyst system. [Kausch, C. M.; Leising, J. E.; Medsker, R. E.; Russell, V. M.; Thomas, R. R.; Malik, A. A., Synthesis, characterization, and unusual surface activity of a series of novel architecture, water-dispersible poly(fluorooxetane)s., *Langmuir,* 2002, 18, 5933-5938.]

Thermal analysis. Standard and temperature modulated DSC (MDSC) starting from sub-ambient temperatures were used to measure the telechelic $T_g$ (Table 2). MDSC experiments were performed at a heating rate of 3° C./min with a modulation temperature of ±0.5° C./min. It is important to note that all telechelics have low glass transition temperatures characteristic of polyols used as soft blocks in polyurethanes.

TABLE 2

Measured and calculated glass transition temperatures of homo and co-telechelics.

| Homo or Co-telechelic Poly(oxetane) | $T_g$ (° C.) (DSC) | $T_g$ (° C.) (Calculated[a]) |
|---|---|---|
| BrOx | −24 | — |
| 3FOx | −51 | — |
| 5FOx | −48 | — |
| 3FOx:BrOx-1:2 | −33 | −32 |
| 3FOx:BrOx-1:1 | −37 | −36 |
| 3FOx:BrOx-2:1 | −38 | −39 |
| 5FOx:BrOx-1:2 | −34 | −33 |
| 5FOx:BrOx-1:1 | −36 | −36 |
| 5FOx:BrOx-2:1 | −39 | −39 |

[a]From the Fox equation.

Polyurethanes containing FOx-BrOx soft blocks. A number of SM polyurethanes were synthesized. The compositions are summarized in Table 3. In designating compositions, such as IPDI-BD(40)/3FOx:BrOx-1:1(4700), the hard block composition is followed with hard block wt % in parentheses. The soft block segmers are next, followed by their mole ratio and $M_n$ in parenthesis. The segmented PUs were synthesized in a conventional two-step procedure as shown in Scheme 2. First, an excess of IPDI was added to telechelic. When all the alcohol groups were consumed, BD chain extender was added until no isocyanate absorption was detectible by FT-IR. As the viscosity increased, DMF or THF/DMF was added so that the solution contained about 30-40% solids at the end of the reaction. PUs having different concentrations of soft block can be obtained simply by changing the ratio of telechelic to chain extender (1,4-butanediol) ratio.

The hard segment concentration was utilized was 40-45 wt %. PUs having lower hard block content (25-35%) are mechanically very soft while those with higher hard block content (45-60%) are rigid. The hard block content in an SM application could thus be varied to optimize compliance with the substrate polymer.

Representative FOx-BrOx polyurethane synthesis. A typical synthesis is represented by the synthesis for IPDI-BD(40)/ 3FOx:BrOx-1:1(4700). The polyurethane (PU) was synthesized in 3-neck round bottom flask. Oxetane polyol, 3FoxBrOx(1:1), (9.23 g, 1.92 mmol) was introduced into the flask with isophorone diisocyanate, IPDI, (4.44 g, 19.97 mmol). Dimethyl formamide, DMF, (3.13 g) was added into the reaction mixture as solvent. The initial % solid was 81%. The solution was heated and stirred with an over-head stirrer under nitrogen purge and with condenser. 7 drops of dibutyltin dilaurate catalyst, T-12, (1 wt % in toluene) was added to reaction medium when the reaction temperature was 65-70° C. The mixture was stirred for 3 hours at this temperature range. The reaction was followed by FT-IR. After 3 hours the prepolymer was ready for chain extension. 1,4 butane diol, BD, (1.61 g, 17.87 mmol) was used as chain extender. The reaction was frequently diluted with DMF as the polymer molecular weight increases. Chain extension took place at the same temperature range (65-70° C.). The reaction was followed with FT-IR. The reaction continued until all the isocyanate (NCO) was consumed. The final PU has slightly yellow color and the final concentration of the mixture was 43%. The resulting PU was then precipitated into methanol for purification. The solution cast PU films were prepared.

Table 3 provides compositions, molecular weights, and DSC information. We were not able to synthesize a 5FOx homo-telechelic polyurethane. The reaction mixture phase separated during the chain extension apparently due to the different solubility parameters of 5FOx

TABLE 3

Molecular weights, and glass transitions temperatures of polyurethanes

| Designation | | $M_n$ (×$10^3$) | $M_w$ (×$10^3$) | PD | $T_g^a$ (ss) | $T_g^b$ (hs) | Phase Sep[c] |
|---|---|---|---|---|---|---|---|
| IPDI-BD(50)/PTMO(2000) | Base PU | 23.3 | 52.5 | 2.26 | −46 | 38 | 0.76 |
| IPDI-BD(40)/BrOx(2800) | PU-1 | 19.4 | 42.9 | 2.21 | −10 | 56 | 0.81 |
| IPDI-BD(40)/3FOx(3400) | PU-2 | 17.5 | 37.4 | 2.14 | −37 | 46 | 0.84 |
| IPDI-BD(40)/3FOx:BrOx-2:1(4700) | PU-3 | 18.9 | 46.0 | 2.43 | −29 | 73 | 0.89 |
| IPDI-BD(40)/3FOx:BrOx-1:1(4700) | PU-4 | 17.9 | 36.8 | 2.05 | −29 | 62 | 0.90 |
| IPDI-BD(40)/3FOx:BrOx-1:2(3400) | PU-5 | 16.5 | 33.9 | 2.06 | −24 | 56 | 0.89 |
| IPDI-BD(40)/5FOx:BrOx-2:1(2500) | PU-6 | 18.9 | 40.1 | 2.12 | −27 | 57 | 0.88 |
| IPDI-BD(40)/5FOx:BrOx-1:1(4100) | PU-7 | 29.6 | 61.2 | 2.07 | −25 | 64 | 0.89 |
| IPDI-BD(40)/5FOx:BrOx-1:2(3400) | PU-8 | 16.6 | 33.8 | 2.04 | −29 | 64 | 0.89 |
| IPDI-BD | Hard Block | 17.2 | 31.8 | 1.85 | NA | 85 | na[d] |

[a]Soft segment (ss) glass transition temperature.
[b]Hard segment (hs) glass transition temperature.
[c]Weight fraction (±0.xx) soft block in the soft-segment phase, calculated by using the Fox equation.
[d]Not applicable.

soft and polyurethane hard blocks.

Molecular weights. Molecular weights, and polydispersities of the new polyurethanes are shown in Table 3. GPC analyses gave $M_w$s in the range of 30-60,000. With one exception, $M_w$s for the FOx:BrOx polyurethanes have somewhat lower $M_w$s compared to the conventional PTMO analog. While molecular weights are modest, all the polyurethanes formed smooth, optically transparent coatings and freestanding films.

Wetting Behavior. Polyurethane wetting behavior was determined by the Wilhelmy plate method using a Dynamic Contact Angle Analyzer (DCA). The Wilhelmy plate experiment has been discussed in connection with the measurement of intrinsic contact angles for model PDMS networks. [Uilk, J. M.; Mera, A. E.; Fox, R. B.; Wynne, K. J., Hydrosilation-cured poly(dimethylsiloxane) networks: Intrinsic contact angles via dynamic contact angle analysis, Macromolecules, 2003, 36, 3689-3694.] Remarkably, all of the co-telechelic polyurethanes have higher $\theta_{adv}$ and lower $\theta_{rec}$ than the parent homo-telechelic PUs (Table 4).

thane containing a 2000 MW poly(tetramethylene oxide) soft block. X-ray photoelectron spectroscopy demonstrated surface concentration of the SM by virtue of Br and F analysis that was similar to IPDI-BD(40)/3FOx:BrOx-1:1(4700) alone. These results demonstrate the efficacy of surface concentration of the reactive C—Br function. That is, a function which contains a Br leaving group that allows modification of the polymer after formation of the polymeric article or coating.

EXAMPLE 2

Monomer synthesis. 3-(Methoxyethoxyethoxymethyl)-3-methyloxetane (ME2Ox) was synthesized using phase transfer catalysis (PTC). A mixture of 2-(2-methoxyethoxy)ethanol (60.1 g, 0.5 mol), BrOx (82.5 g, 0.5 mol), TBAB (8.0 g, 0.025 mol) and water (20 ml) was stirred and heated to 75° C. Then, a solution of KOH (35.5 g, 87%, 0.55 mol) in water (50 ml) was added. The reaction mixture was stirred vigorously at 80-85° C. for 7 hrs. The mixture was cooled to room tempera-

TABLE 4

Advancing and receding contact angles for PUs.

| PU(ratio)[a] | Cycle-1 Adv/Rec | Cycle-2 Adv/Rec | Cycle-3 Adv/Rec | Cycle-4 Adv/Rec | Cycle-5 Adv/Rec | Water Con. |
|---|---|---|---|---|---|---|
| Base PU | 84/55 | 82/55 | 82/56 | 81/56 | 81/56 | No |
| PU-1 | 102/42 | 101/41 | 101/41 | 101/40 | 101/40 | No |
| PU-2 | 105/45 | 99/45 | 98/46 | 98/46 | 98/46 | Yes |
| PU-3 (2:1) | 108/35 | 108/35 | 108/35 | 108/34 | 108/34 | No |
| PU-4 (1:1) | 116/33 | 115/32 | 116/32 | | | No |
| PU-5 (1:2) | 104/34 | 102/34 | 102/34 | 102/34 | 102/34 | Yes |
| PU-6 (2:1) | 109/38 | 108/38 | 108/38 | 108/38 | 108/38 | No |
| PU-7 (1:1) | 109/35 | 109/35 | 109/35 | 109/35 | 109/35 | Yes |
| PU-8 (1:2) | 107/36 | 106/36 | 106/36 | 106/36 | 106/36 | Yes |

[a]Ratio of nFOx:BrOx. n = 3 for PU-3, 4, and 5. n = 5 for PU-6, 7, and 8.

The most surprising result for PU co-telechelics ($\theta_{adv}$, 116°; $\theta_{rec}$, 32°) is the wetting behavior of PU-4, IPDI-BD (40)/3FOx:BrOx-1:1(4700). These values are constant over three cycles and no water contamination is detected. The very stable contact angle hysteresis (84°) is noteworthy for topologically smooth surfaces (vida infra). Few polymers have $\theta_{adv}$ that exceed 116°.

Surface Modifying Behavior. IPDI-BD(40)/3FOx:BrOx-1:1(4700) (2%) was added to an ordinary IPDI-BD polyureture, filtered, and diluted with water. The product was extracted with methylene chloride and distilled at 100° C./8 mmHg. ME2Ox monomer; $^1$H-NMR (CDCl$_3$) δ1.32 (—CH$_3$, 3H, s), δ3.39 (—OCH$_3$ 3H, s), δ3.55 (—OCH$_2$CH$_2$O—, 4H, m), δ3.67 (—OCH$_2$CH$_2$O—, 4H, and —CH$_2$—, 2H, m), δ4.35 (ring —CH$_2$—, 2H, d), δ4.52 (ring CH$_2$, 2H, d); $^{13}$C-NMR (CDCl$_3$) δ21.5 (—CH$_3$), δ40.0(—C—), δ59.1 (—OCH$_3$), δ70.7, 71.1, and 72.1 (—OCH$_2$CH$_2$O—), δ76.6 (—CH$_2$—), δ80.2 (ring —CH$_2$—).

7FOx monomer was prepared from BrOx and 2,2,3,3,4,4,4-heptafluorobutanol by the same procedure used for ME2Ox monomer. 7-FOx monomer; $^1$H-NMR (CDCl$_3$) $\delta$1.31 (—CH$_3$, 3H, s), $\delta$3.67 (—CH$_2$—, 2H, s), $\delta$3.99 (—CH$_2$CF$_2$—, 2H, t), $\delta$4.34 (ring —CH$_2$—, 2H, d), $\delta$4.50 (ring —CH$_2$—, 2H, d).

Homo- and Cotelechelic polyoxetane synthesis. Homo- and copolymerization of ME2Ox and FOx monomers were carried out by a modification of a published procedure for FOx and methyloxetane. [Malik, A. A.; Archibald, T. G.; GenCorp: US, 2000.] The homotelechilic has not been previously synthesized and is a new composition of matter. Cationic ring opening polymerization 3-bromomethyl-3- was employed using BF$_3$ and 1,4-butanediol as catalyst and co-catalyst, respectively. Methylene chloride (10 ml) was poured into a round bottom flask under nitrogen. 1,4-butanediol (165 mg, 1.84 mmol) and BF$_3$—OEt$_2$ (520 mg, 3.67 mmol) in methylene chloride (10 ml) were added and stirred at room temperature for 45 min under nitrogen. Then the solution was cooled to 0-5° C. in ice bath, and a mixture of ME2Ox and FOx monomers (e.g., total 36.7 mmol) in methylene chloride (10 ml) was added dropwise at the rate of 0.5 ml/min. The reaction was kept at 0-5° C. for 4 hrs with stirring. The reaction mixture was then brought to room temperature and quenched with 30 ml of water. The organic phase was separated, washed with 0.2% HCl and NaCl aqueous solution and then solvent was evaporated. The product (a viscous, opaque liquid) was re-dissolved in acetone, and re-precipitated in water. The resulting viscous liquid was separated and dried in a vacuum oven at 70° C., 5 Torr overnight to give a transparent oily product with >80% yield.

ME2Ox homopolymer; $^1$H-NMR (CDCl$_3$) $\delta$0.91 (—CH$_3$, 3H, s), $\delta$3.19 (backbone —CH$_2$—, 4H, m), $\delta$3.30 (—CH$_2$—, 2H, s), $\delta$3.38 (—OCH$_3$ 3H, s), $\delta$3.55 (—OCH$_2$CH$_2$O—, 4H, m), $\delta$ 3.64 (—OCH$_2$CH$_2$O—, 4H, m); $^{13}$C-NMR (CDCl$_3$) $\delta$17.3-17.9 (—CH$_3$), $\delta$40.8-41.3 (backbone —C—), $\delta$58.9 (—OCH$_3$), $\delta$70.4 and 71.9 (—OCH$_2$CH$_2$O—), $\delta$70.9-71.3 (—CH$_2$—), $\delta$74.0 (backbone —CH$_2$—).

ME2Ox/5FOx (ME2Ox/7FOx) copolymer; $^1$H-NMR (CDCl$_3$) $\delta$0.91 (—CH$_3$ for ME2Ox and FOx, 3H, s), $\delta$3.19 (backbone —CH$_2$—, 4H, m), $\delta$3.30 (—CH$_2$— for ME2Ox, 2H, s), $\delta$3.38 (—OCH$_3$ 3H, s), $\delta$3.44 (—CH$_2$— for FOx, 2H, s), $\delta$3.55 (—OCH$_2$CH$_2$O—, 4H, m), $\delta$3.64 (—OCH$_2$CH$_2$O—, 4H, m), $\delta$3.85 (—CH$_2$CF$_2$—, 2H, t); $^{13}$C-NMR (CDCl$_3$) $\delta$16.9-17.8 (—CH$_3$ for ME2Ox and FOx), $\delta$40.8-41.5 (backbone —C—), $\delta$58.6 (—OCH$_3$), $\delta$68.0 (—CH$_2$CF$_2$—, t), $\delta$70.4 and 71.9 (—OCH$_2$CH$_2$O—), $\delta$70.9-71.3 (—CH$_2$— for ME2Ox), $\delta$73.4 (backbone —CH$_2$— for FOx), $\delta$74.0 (backbone —CH$_2$— for ME2Ox), $\delta$75.3 (—CH$_2$— for FOx), $\delta$110.0-123.3 (—CF$_n$CF$_3$).

Table 5 lists the molar ratios of monomer feed as well as the compositions of polymers. Monomer/1,4-butanediol ratios were varied in order to make polyoxetanes with differing molecular weights. The degree of polymerization (D$_p$) and equivalent molecular weight are determined by end group analysis as described above. The BF$_3$—OEt$_2$/1,4-butanediol ratio was kept constant at 2.2/1, and in all compositions in Table 5, the reactions were done under nitrogen atmosphere with a temperature at 0-5° C. Monomer ratios in copolymers are very close to feed ratios.

GPC results are also listed in Table 5. The number average molecular weights (M$_n$) correlate well with end group analysis results for ME2Ox homo- and ME2Ox/FOx copolymers, but show higher values for 5FOx homopolymer. The molecular distribution has a trend that the polydispersity (M$_w$/M$_n$) decreases as monomer/co-catalyst ratio increases for all polymer series. When the monomer/co-catalyst ratio is above 22, the polydispersities are 1.9-2.2. As shown in Table 5, the D$_p$ of polymer is not directly related to the monomer/co-catalyst ratios.

TABLE 5

Copolymerization of ME2Ox and FOx monomers via BF$_3$—OEt$_2$ catalyst system at 0° C. in methyene chloride

| Sample Name | Monomer feed ratio | | | [Monomer]/ [co-catalyst]$^a$ | ME2Ox/ FOx | D$_p^b$ | Polymers Equiv. MW$^b$ | M$_n^c$ (/10$^3$) | M$_w$/M$_n^c$ |
|---|---|---|---|---|---|---|---|---|---|
| | ME2Ox | 5FOx | 7FOx | | | | | | |
| M-1 | 1 | — | — | 5.5 | — | 12.4 | 2540 | 3.4 | 2.7 |
| M-2 | 1 | — | — | 11 | — | 16.9 | 3450 | 3.6 | 3.2 |
| M-3 | 1 | — | — | 22 | — | 18.6 | 3810 | 3.0 | 2.1 |
| M-4 | 1 | — | — | 33 | — | 18.2 | 3710 | 3.3 | 2.2 |
| M5F-1 | 0.5 | 0.5 | — | 5.5 | 0.53/0.47 | 16.8 | 3680 | 4.0 | 2.6 |
| M5F-2 | 0.5 | 0.5 | — | 11 | 0.54/0.46 | 17.9 | 3910 | 4.8 | 2.8 |
| M5F-3 | 0.5 | 0.5 | — | 22 | 0.53/0.47 | 20.8 | 4570 | 4.7 | 1.9 |
| M5F-4 | 0.5 | 0.5 | — | 33 | 0.52/0.48 | 20.6 | 4520 | 4.8 | 1.9 |
| F-1 | — | 1 | — | 5.5 | — | 20.1 | 4720 | 8.7 | 2.4 |
| F-2 | — | 1 | — | 11 | — | 27.3 | 6390 | 11.6 | 2.1 |
| F-3 | — | 1 | — | 22 | — | 31.9 | 7470 | 11.8 | 1.9 |
| F-4 | — | 1 | — | 33 | — | 36.8 | 8620 | 12.9 | 2.0 |
| M7F-1 | 0.5 | — | 0.5 | 22 | 0.55/0.45 | 18.6 | 4550 | 5.3 | 2.2 |
| M7F-2 | 0.67 | — | 0.33 | 22 | 0.66/0.34 | 14.9 | 3440 | 4.5 | 1.9 |

$^a$Monomer to co-catalyst (1,4-butanediol) molar ratio, [BF$_3$—OEt$_2$]/[1,4-butanediol = 2.2 (constant)
$^b$Determined by $^1$H-NMR end group analysis
$^c$Determined by GPC Thermal analysis. Glass transition temperatures (T$_g$'s) of the polyoxetanes were measured using sub-ambient DSC. Table 6 shows T$_g$ of ME2Ox and FOx homopolymers and their copolymers. ME2Ox homopolymer has the lowest T$_g$ (-67° C.) close to the T$_g$ of PTMO (ca, -70° C.).

TABLE 6

Glass transition temperatures (Tg) for polyoxetanes

| Homo- or Copolymers | Tg (° C.) |
|---|---|
| ME2Ox | −67.3 |
| 5FOx | −43.5 |
| 7FOx | −52.7 |
| ME2Ox/5FOx (1/1) | −56.9 |
| ME2Ox/7FOx (1/1) | −55.6 |
| ME2Ox/7FOx (2/1) | −58.3 |

The $T_g$ of 5FOx homopolymer is approximately −44° C. From a scan of physical mixture of ME2Ox and 5FOx homopolymers, it was observed that this mixture has two $T_g$'s because the two homopolymers are completely immiscible. In contrast, ME2Ox/5FOx (1/1) copolymer gives one $T_g$ at −57° C. in between the $T_g$'s of the homopolymers. This result supports the composition study of the copolymer that indicates a random or alternating tendency but not blocky sequence. The $T_g$ of copolymer can be estimated by the Fox equation using the T's of homopolymers:

$$T_{g(cal)}^{-1} = w_1 T_{g1}^{-1} + w_2 T_{g2}^{-1}$$

where $w_1$ and $w_2$ are weight fraction of each component. Using $w_{(ME2Ox)}$ and $w_{(5FOx)}$ and homopolymer $T_g$s, $T_{g(cal)}$ is −54° C. for ME2Ox/5FOx (1/1). Similarly, $T_{g(cal)}$ of ME2Ox/7FOx (1/1) and ME2Ox/7FOx (2/1) are −58 and −60° C., respectively. Calculated $T_g$s are close to those observed.

EXAMPLE 3

As a further example for synthesis of telechelics, FOx-MEnOx telechelics were prepared where n=3 or 7. The purpose of this synthetic work was to provide F-2/F-3 groups that would have a more hydrophilic character. In short, using ring opening polymerization as described above, polyoxetane telechelics with hydrophobic semifluorinated and hydrophilic oligoalkylether pendant groups have been synthesized with random and block sequences. Polyurethanes incorporating these novel telechelics as soft blocks have also been prepared. For the first time, the effect of soft block sequence distribution on polyurethane surface morphology and wetting behavior has been demonstrated. TM-AFM reveals surface nanophase separation for the polyurethane containing a block-oxetane co-telechelic, while the polyurethane containing a random-oxetane soft block shows no surface microstructure. Wetting behavior is strongly influenced by the surface nanoscale morphology. This observation suggests that surface nanostructure must be taken into account for demanding applications such as those requiring biocompatibility or "smart" behavior.

The reaction mechanism of cationic ring-opening polymerization (ROP) of oxetane monomers using boron trifluoride ($BF_3$) has seen considerable study and the general features are known as described above. In the present work, modified reaction conditions were used to give telechelics having different monomer sequences. The goal of this work was to learn whether monomer sequence distribution would affect surface properties of derived polyurethanes.

The oxetane monomer 3-(2,5,8,11-tetraoxydodecyl)-3-methyloxetane (ME3Ox), a new compound, was synthesized from tri(ethylene glycol) monomethyether and 3-bromomethyl-3-methyloxetane (BrOx). Copolymerization of ME3Ox and 3-trifluoroethoxymethyl-3-methyloxetane (3FOx) were carried out by cationic ring opening polymerization using $BF_3$ and butane diol co-catalysts. For the preparation of block copolyoxetane ME3Ox-block-3FOx, ME3Ox monomer was added to catalyst at 0° C. for 4 hrs. Then a dilute solution ($CH_2Cl_2$) of 3FOx monomer was added dropwise slowly over 24 hrs. The reaction mixture was stirred more 12 hrs, then quenched with water and the product isolated.

To obtain a blocky-type copolymer, monomer addition order and addition speed were varied. When 3FOx monomer was polymerized first in the presence of $BF_3$—$OEt_2$ and butane diol (BD) cocatalysts and the second monomer ME3Ox was added, a mixture of homo-telechelics as a two-phase liquid mixture was obtained. Interestingly, when ME3Ox was added as the first monomer followed by 3FOx, the product was a one phase viscous liquid, indicating formation of a block copolymer (telechelic). After the reaction of first monomer ME3Ox, Mn determined by end group analysis with trifluoroacetic anhydride is 2,600. Then, after slow addition of second monomer 3FOx, Mn=4,200 for the final telechelic. A parallel increase in Mw by GPC was obtained. Table 7 contains compositions and characterization data.

TABLE 6

| Telechelic polymers | Endgp (10⁻³) | GPC molecular weight (10⁻³) | | | | DSC | | MDSC |
|---|---|---|---|---|---|---|---|---|
| | | Mn | Mw | (Pd) | cyc % | Tg | Tc/Tm | Tg¹ |
| PTMO | 2.2 | 3.7 | 6.8 | 1.9 | | ? | ? | −78.1 |
| 3FOx homo | 7.1 | 13.9 | 21.6 | 1.5 | 20 | −47.6 | — | −47.4 |
| 5FOx homo | 7.5 | — | — | — | — | −45.9 | — | — |
| 7FOx homo | — | — | — | — | — | −54.6 | — | — |
| ME2Ox homo | 3.8 | 3.0 | 6.3 | 2.1 | — | −68.0 | — | — |
| ME2Ox/3FOx (1/1) | 3.8 | 2.3 | 7.5 | 3.2 | — | −57.7 | — | — |
| ME2Ox/5FOx (1/1) | 4.6 | 4.7 | 8.9 | 1.9 | — | −58.1 | — | — |
| ME2Ox/7FOx (1/1) | 4.5 | 7.5 | 12.6 | 1.7 | — | −56.9 | — | — |
| ME2Ox/7FOx (2/1) | 3.4 | 6.1 | 9.6 | 1.6 | — | −58.5 | — | — |
| ME3Ox homo | 3.0 | 0.7 | 3.2 | 4.6 | — | −75.8 | — | −74.2 |
| ME3Ox/3FOx (1/1) | 3.1 | 1.6 | 4.3 | 2.6 | 12 | −63.9 | — | −61.8 |
| ME3Ox-block-3FOx (2/3) | 4.2 | 1.6 | 4.1 | 2.6 | 9 | −61.8 | — | −59.7 |
| ME3Ox-block-3FOx (2/1) | 1.9 | 0.8 | 3.5 | 4.5 | — | −70.7 | — | −69.0 |
| ME7Ox homo | 3.2 | 1.0 | 2.7 | 2.7 | — | −71.8 | −52/−16 | — |
| ME7Ox/3FOx (1/1) | 5.8 | 2.4 | 5.1 | 2.1 | — | −66.9 | −30/−16 | — |
| ME7Ox-block-3FOx (2/3) | 5.2 | 3.2 | 5.2 | 1.6 | — | −64.8 | −28/−13 | — |
| ME7Ox-block-3FOx (2/1) | 3.5 | 1.9 | 4.5 | 2.4 | — | −70.5 | −48/−16 | — |
| ME2Ox homo + 5FOx homo | — | — | — | — | — | −64/−45 | — | — |
| ME3Ox homo + 3FOx homo | — | — | — | — | — | — | — | −69.8/−57.9 |

TABLE 6-continued

| Polyurethanes | ss wt % | molecular weight (10⁻³) | | | DSC | | MDSC | |
| --- | --- | --- | --- | --- | --- | --- | --- | --- |
| | | Mn | Mw | Pd | Tg$^1$ | Tg$^2$ | Tg$^1$ | Tg$^2$ |
| PTMO/MDI/BD | 64 | 37.5 | 142.9 | 3.8 | ? | ? | −70.3 | 56.6 |
| (ME2Ox homo)/MDI/DB | 50 | — | — | — | (?) | 49.7 | — | — |
| (ME2Ox/3FOx (1/1)/MDI/DB | 74 | — | — | — | 38.8 | (?) | — | — |
| (ME2Ox/5FOx (1/1)/MDI/DB | 74 | — | — | — | −41.8 | (?) | — | — |
| (ME2Ox/5FOx (1/1)/MDI/DB | 45 | — | — | — | — | — | — | — |
| (ME3Ox homo)/MDI/DB | 63 | 7.8 | 14.1 | 1.8 | −43.8 | (?) | −36.8 | 129.9? |
| (ME3Ox/3FOx (1/1)/MDI/DB | 73 | 9.1 | 24.3 | 2.7 | −41.2 | (?) | −36.8 | ? |
| (ME3Ox-b-3FOx (2/3)/MDI/DB | 68 | 7.4 | 15.2 | 2.1 | −41.9 | (?) | −38.4 | 65.1 |
| (ME7Ox homo)/MDI/DB | 69 | 6.5 | 10.0 | 1.6 | −55.9 | (?) | — | — |
| (ME7Ox/3FOx (1/1)/MDI/DB | 58 | 6.0 | 10.1 | 1.7 | −46.9 | (?) | — | — |
| (ME7Ox-b-3FOx (2/3)/MDI/DB | 66 | 6.3 | 12.3 | 2.0 | −44.4 | (?) | — | — |
| (3FOx homo)/MDI/DB | 71 | 13.4 | 43.1 | 3.2 | — | — | −39.9 | 59.9 |
| (Mix.ME3Ox + FOx)(1/1)/MDI/DB | 70 | 7.9 | 16.0 | 2.0 | — | — | −59.3/−42.5 | ? |

GPC molecular weight determinations on telechelics usually showed the presence of a peak corresponding to cyclic tetramers. [Malik, A. A.; Archibald, T. G.; GenCorp: US, 2000] The percent cyclics present in the present work (0-20%) is not reproducible. Samples examined by DSC and $^{19}$F-NMR contained cyclics but the qualitative conclusions are deemed valid. Furthermore, once telechelics are used to prepare PUs, cyclics are removed by purification procedures, as the telechelics are nonfunctional and relatively nonpolar.

To investigate structural differences, $^{19}$F-NMR spectra were obtained. The 3FOx CF$_3$— peaks in block and random copolymers shift to low field relative to 3FOx homopolymer. A similar small chemical shift is observed when ME3Ox homopolymer is admixed with 3FOx homopolymer solutions, indicating the shift for copolymers is largely a solvent effect. A comparison of the relative peak shapes is revealing. Homo- and block-telechelics show a series of well-resolved peaks with $J_{1H-19F}$=8 Hz. In contrast, the random copolymer peak is broad with little resolvable structure. This observation supports the hypothesis that the random telechelic is comprised of random sequences with many sequence distributions. In contrast, the block co-telechelic contains (3-FOx)$_n$ sequences that mimic those in the homo-telechelic. Hence 3FOx and ME3Ox-block-3FOx telechelics have similar $^{19}$F-NMR spectra.

Polyurethanes were prepared using polyoxetane telechelics or a reference PTMO soft segment as described above for ME2Ox and FOx-BrOx telechelics. In brief, methylenediphenyldiisocyanate (MDI) and butane diol (BD) were used for hard segment with ME3Ox/3FOx copolymer soft segment. Polyurethanes were prepared via solution reaction in dimethylacetoamide (DMAc) using a two-step method (first, MDI plus soft block telechelic; second, BD chain extender). Poly(tetramethylene oxide) (PTMO), M$_n$=2,000, was used as soft block for a standard segmented polyurethane as a control sample.

Figure 8:
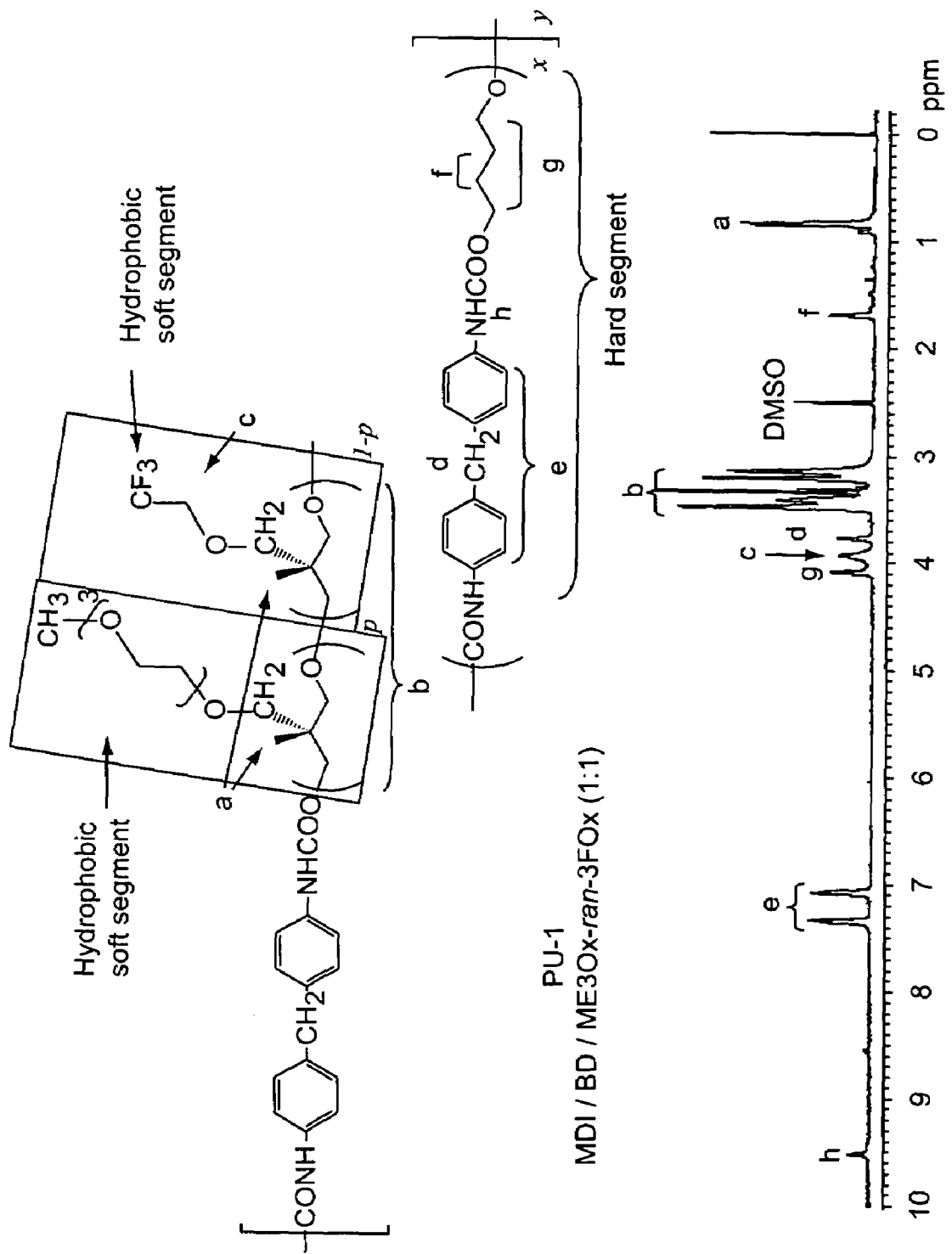
FIG. 8 shows the chemical structure and $^1$H-NMR spectrum of PU-1 containing ME3Ox-ran-3FOx copolymer soft segment in DMSO-d6.

FIG. 8 shows the structure and H-NMR spectrum of a representative PU, MDI/BD(27)/ME3Ox-ran-3FOx(1:1), PU-1 in DMSO-d6. Polyurethanes are designated: isocyanate/chain extender (hard segment wt %)/soft segment monomer 1-sequence-soft segment monomer 2 (mole ratio). Other compositions were also determined by $^1$H-NMR spectra: MDI/BD(32)/ME3Ox-block-3FOx(2:3), PU-2, and MDI/BD (36)/PTMO, PU-3. Glass slides were dip-coated from 20% DMAc solutions. The dip-coated PU films were prepared on glass slides from 20% dimethylacetamide (DMAC) at room temperature, dried at 60° C. for 5 h at ambient pressure, followed at 80° C. for 2 days under vacuum.

Figure 9:
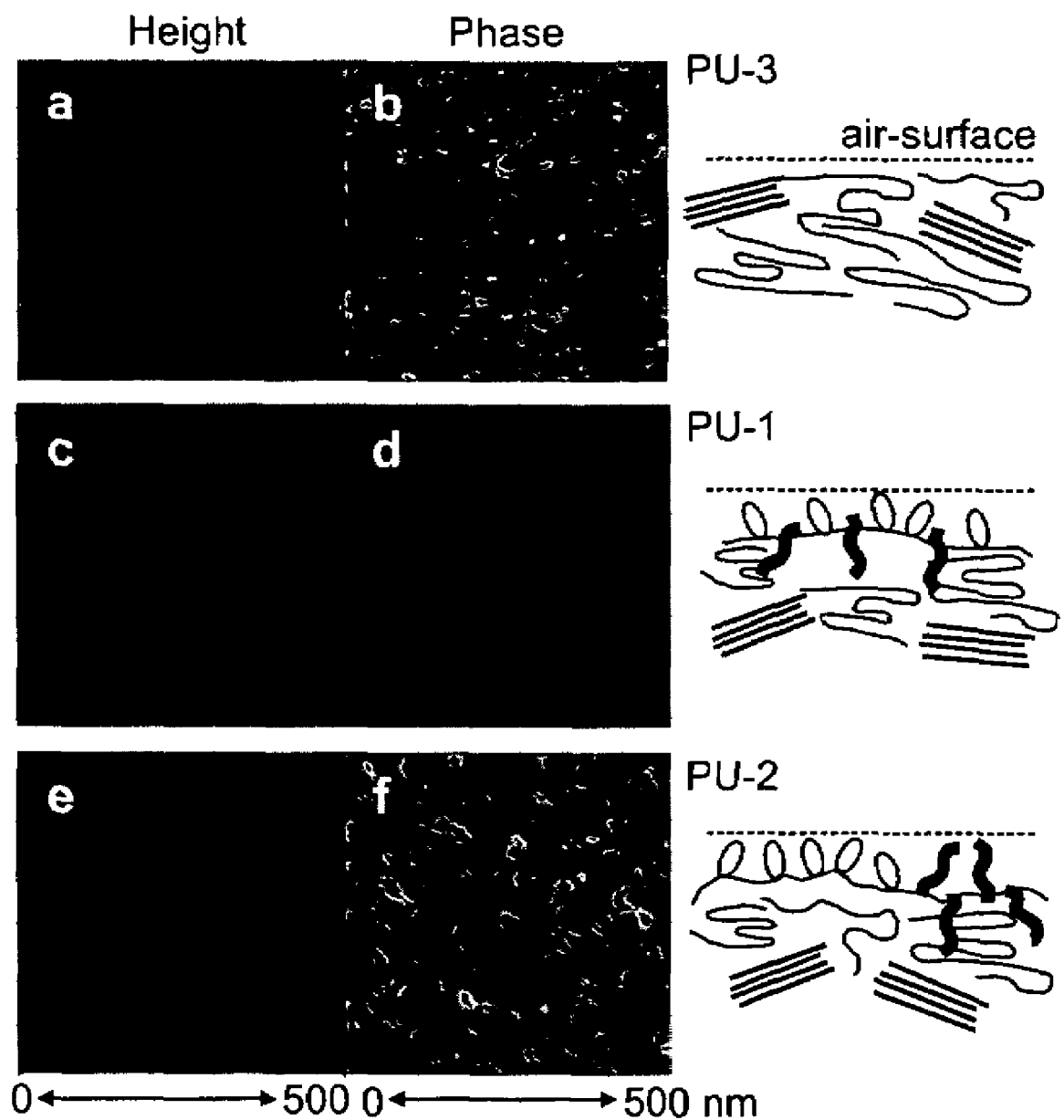
FIG. 9a-f show typical tapping-mode AFM images of polyurethane films. PU-3: containing PTMO (a,b), PU-1: containing ME3Ox-ran-3FOx (c,d), and PU-2: containing ME3Ox-block-3FOx (e,f); (a,c,e): height images at z=10 nm, and (b,d,f): phase images at z=20°; Rms: (a) 0.6 nm, (c) 0.3 nm, and (e) 0.9 nm; Tapping force (A/A$_0$): (a,b) 0.87, (c,d) 0.83, and (e,f) 0.92.

Tapping-mode AFM (TM-AFM) is a powerful method for evaluating polymer surface morphology. FIGS. 9a-f show TM-AFM images of PU films containing PTMO (PU-3), ME3Ox-ran-3FOx copolymer (PU-1), and ME3Ox-block-3FOx copolymer (PU-2). The surfaces of all films are topologically quite flat (FIGS. 9a, c, e) with RMS roughness (R$_q$) less than 1 nm. Phase images of the three films are clearly different (FIGS. 9b, d, f). Although tapping forces are relatively weak (A/A$_0$=0.83-0.92), phase images for PU-3 (FIG. 9b) and PU-2 (FIG. 9f) show strong contrast characteristic of nanoscale phase separation.

The surface of PU-3 (FIG. 9b) has phase separation on the order of 10 nm due to the hard and soft segments as shown schematically. This typical PU phase segregation has been observed previously. [Garrett, J. T.; Siedlecki, C. A.; Runt, J. Macromolecules 2001, 34, 7066-7070] The phase image of PU-1 containing the ME3Ox-ran-3FOx telechelic is featureless (FIG. 9d). This is consistent with a surface structure where the random-soft block predominates. With increased tapping force (A/A$_0$=0.5-0.6) a phase-separated structure appears in the phase image (data not shown), reflecting the presence of sub-surface hard blocks.

In contrast, TM-AFM of PU-2 containing the block-soft segment (FIG. 9f) shows strong nano-phase separation that is attributed to two block domains, viz., ME3Ox and 3FOx. We use a conventional interpretation of modulus-sensitive phase images at light tapping where the lighter color portions are assigned to the organized domain, in this case 3FOx. [Uilk, 2002 #533] The average domain size is about 20 nm in diameter, larger than the hard- and soft-segment segregation observed in PU-3 (FIG. 9b). The observed phase separation must reflect the immiscibility of the 3FOx and ME3Ox block segments in the liquid phase, as the blocks are 75° C. (3FOx) and 100° C. (ME3Ox) above T$_g$.

The interesting difference in nanoscale surface phase separation for PUs containing random and block co-telechelics is reflected in contrasting wetting behavior. For evaluation of surface wetting properties, dynamic contact angle (DCA) analysis by the Wilhelmy plate method was used as described in Uilk, J. M.; Mera, A. E.; Fox, R. B.; Wynne, K. J. Macromolecules 2003, 36, 3689-3694.] The RMS roughness, R$_q$, is less than 1 nm for all coatings. Thus surface roughness cannot contribute to advancing (θ$_{adv}$) or receding (θ$_{rec}$) contact angles or contact angle hysteresis (delta θ).

As a point of reference, PU-3 containing the PTMO soft segment was examined. PU-3 has a θ$_{adv}$ of 93° and θ$_{rec}$ of 49°. From previous work [Lamba, N. M. K.; Woodhouse, K. A.; Cooper, S. L. In Polyurethanes in Biomedical Applications;

CRC Press: Boca Raton, Fla., 1998, p 15.] and our experience, $\theta_{adv}$, $\theta_{rec}$, and delta $\theta(44°)$ are fairly typical values for PTMO PUs. The moderate delta $\theta(44°)$ is largely attributed to rapid surface reorganization of the low $T_g$ PTMO soft block, though TM-AFM suggests there may be a near-surface hard block contribution as well.

One approach to analysis of chemically heterogeneous surfaces using wetting behavior is to compare an "AB" surface to that of A and B alone. Several well-known methods exist to analyze nonideality responsible for surface behavior. Here, we use a qualitative comparison of cotelechelic PUs with corresponding homo-telechelic PUs. Homo-telechelic compositions and contact angles are: MDI/BD(29)/3FOx: $\theta_{adv}$, 110°, $\theta_{rec}$, 70°; MDI/BD(37)/ME3Ox; $\theta_{adv}$, 93°, $\theta_{rec}$, 32°.

Analysis of PU-1 containing the ME3Ox-ran-3FOx soft segment gave $\theta_{adv}$=104°, $\theta_{rec}$=39°, and delta $\theta$=65°. The PU-1 surface is hydrophobic in air due to fluorinated groups with $\theta_{adv}$ similar to the PU 3FOx homopolymer. However, PU-1 is hydrophilic in water ($\theta_{rec}$, 39°) with a receding contact angle closer to ME3Ox PU (32°) than to 3FOx PU (70°). Clearly, extensive surface reorganization occurs in water favoring hydrophilic ether side groups at the water polymer interface. The result is a very large contact angle hysteresis.

For PU-2 containing ME3Ox-block-3FOx, $\theta_{adv}$ (106°) is also close to $\theta_{adv}$ for the PU 3FOx homopolymer. In this regard, PU-2 and PU-1 are similar. However, $\theta_{rec}$ (56°) is 17° higher than PU-1 ($\theta_{rec}$, 39°) resulting in a smaller contact angle hysteresis for PU-2 (50°) compared to PU-1 (65°). This result indicates the PU-2 surface is hydrophobic in air like the PU 3FOx homopolymer and only moderately hydrophilic in water, more like the PU 3FOx homopolymer than PU ME3Ox. Clearly, the nanophase separated PU-2 surface structure is more hydrophobic overall than the corresponding random-soft block surface. This amplification of hydrophobicity occurs for PU-2 even though the fluorinated nanodomains do not cover the whole surface (TM-AFM, FIG. 9f). Over the limited time scale investigated thus far, the self-assembly responsible for fluorinated surface nanodomains apparently inhibits access of a significant fraction of near-surface, more hydrophilic polyether side chains to water.

This Example demonstrates for the first time, the effect of soft block sequence distribution on surface morphology and wetting behavior. Surface nanophase separation is observed for PU-2, which contains a block-oxetane co-telechelic, while PU-1, which contains a random oxetane co-telechelic, shows no surface microstructure. Surprisingly, wetting behavior is strongly influenced by nanoscale surface morphology. This observation suggests that surface nanostructure must be taken into account for demanding applications such as those that require biocompatibility or "smart" behavior.

Figure 10:
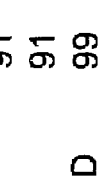
FIG. 10 shows AFM images in combination with contact angle and XPS data which demonstrate the phase separated nanoscale morphology of MDI/BD/(ME3Ox-block-3F)(1:1), PU-2 shown in FIG. 9f is conferred at a 2% loading level to conventional MDI/BD(36)/PTMO polyurethane.

Surface Activity of MeNOx/FOx polyurethanes. While the surface properties of the SM's are interesting by themselves, a key question is "will surface properties be conferred to a substrate polymer". FIG. 10 shows a striking example of conferring surface properties to a substrate polymer. Here, only 2% MDI/BD/(ME3Ox-ran-3FOx)(1:1) (PU-1) and 2% MDI/BD/(ME3-block-3FOx)(1:1), PU-2 respectively are added to a typical base polyurethane, MDI/BD(36)/PTMO. FIG. 10 unequivocally shows that the phase separated nanoscale morphology of MDI/BD/(ME3Ox-block-3F)(1:1), PU-2 seen in FIG. 9f is conferred at a 2% loading level to the conventional MDI/BD(36)/PTMO polyurethane. Wetting behavior on the 2% modified material (shown only for the parent PU-2) is similar to the parent PU-2 and confirms that the SM PU-2 is surface concentrated. Furthermore, X-ray photoelectron spectroscopy confirms the presence of a high level of fluorine in the top 30 nm, consistent with a high 3FOx-like concentration.

In contrast, at a loading of 2% PU-1, MDI/BD/(ME3Ox-ran-3FOx)(1:1) loading level to the conventional MDI/BD (36)/PTMO polyurethane, a relatively featureless nanoscale morphology is seen, as for the parent MDI/BD(27)/ME3Ox-ran-3FOx(1:1), PU-1 (FIG. 9d). Wetting behavior on the 2% modified material (shown only for the parent PU-1) is similar to the parent PU-1 and confirms that the SM PU-1 is surface concentrated. Furthermore, X-ray photoelectron spectroscopy confirms the presence of an intermediate level of fluorine in the top 30 nm, consistent with a higher functional group (F2, hydrophilic MEnOx) concentration.

These results are of the utmost importance in demonstrating that the SM indeed modifies the surface of the commodity-like, conventional MDI/BD(36)/PTMO polyurethane. Importantly, the wetting behavior of the conventional MDI/BD(36)/PTMO polyurethane is modified by 2% incorporation of the SMs in the manner expected (data not shown).

EXAMPLE 4

Reaction on polymer example: substitution of 5,5-dimethyl hydantoin onto IPDI-BD(40)/3FOx:BrOx-1:1(4700), PU-4, from Example 1, Table 3. The substitution reaction was carried out in dimethyl formamide (DMF). 5,5-Dimethyl hydantoin, DMH, (2.55 g, 19.90 mmol) was introduced into 3-neck round bottom flask with DMF (15.30 g). Then potassium carbonate, $K_2CO_3$, (11.06 g, 80.02 mmol) was added into the medium. $K_2CO_3$ is not soluble in DMF; it was suspended in the solvent. The mixture was heated and stirred (stirring bar) under nitrogen purge and with condenser for 1 hour. Then PU (12.27 g, 0.26 mmol) in DMF (21.01 g) was added to reaction medium drop wise. The reaction temperature was kept around 90-95° C. for 42 hours. The reaction was then terminated by cooling to room temperature. The mixture was precipitated into methanol/water (4:1) solution in order to get the final product. The resulting polyurethane was precipitated out of the solution. The degree of substitution and final yield was obtained by NMR (about 70%).

This polyurethane SM is designated 36 in FIG. 7. We refer to the material obtained by treatment of a coating of 36 alone with bleach as 36B. We refer to the composition obtained by adding 2% 36 to the bulk PU 42. First, we consider the remarkable properties of 36 alone.

Figure 11:
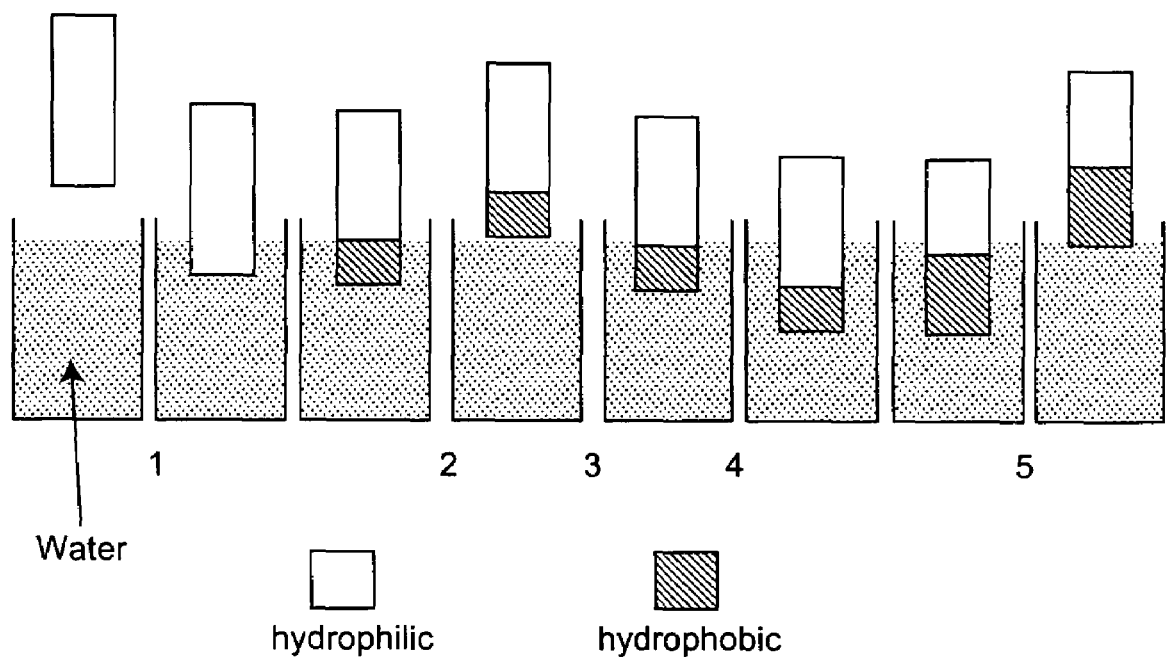
FIG. 11 is a schematic drawing showing the contraphilic properties of SMs of the present invention.

As shown in FIG. 11, coatings designated as 36 in FIG. 7 have unexpectedly unprecedented wetting behavior. All prior art demonstrates that polymers exposed to water either have no change in wetting behavior (e.g., polyethylene, polypropylene, poly(tetrafluoroethylene) due to total lack of interaction with water, or else become apparently more hydrophilic. The latter behavior is found for polymers that have some interaction with water such as nylons and polyurethanes. [Pike, J. K.; Ho, T.; Wynne, K. J., Water-induced surface rearrangements of poly(dimethylsiloxane-urea-urethane) segmented block copolymers, *Chemistry of Materials,* 1996, 8, 856-860.]

Figure 12:
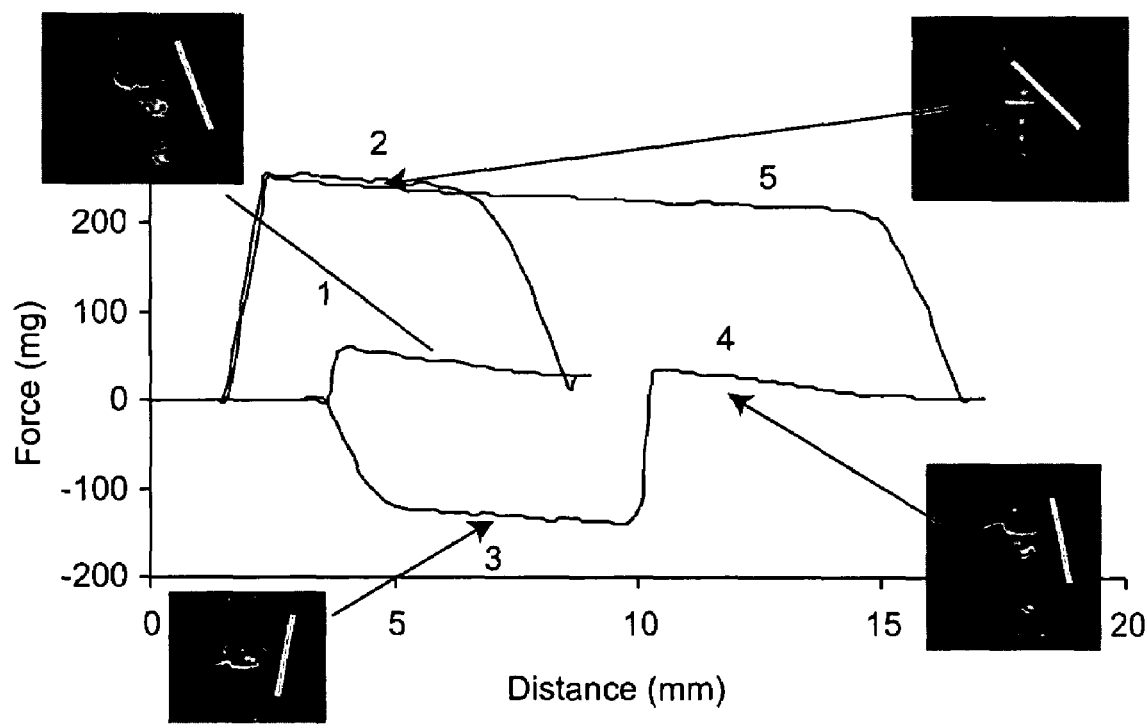
FIG. 12 is a composite of photographs and a graph showing force versus distance for contraphilic polyurethane containing hydantoin substituted poly(oxetane) soft blocks.

As shown in FIG. 11, a coating of 36 becomes more hydrophobic when dipped in water or, if dry initially, becomes more hydrophobic if exposed to a humid atmosphere. FIG. 11 shows a procedure devised to demonstrate the new "contraphilic" behavior. FIG. 12 shows the Wilhelmy plate data and, for simplicity, the visually determined wetting behavior using the conventional sessile drop method. In this case, a picture of the drop was taken (on a separate but identical sample) at important points in the procedure to illustrate the unprecedented contraphilic behavior.

Stage 1. With reference to FIGS. 11 and 12, Stage 1 is the first contact of water with the coating. Observation of the shape of the drop with the contact angle less than 90 degrees illustrates that the coating is hydrophilic. This is quantitatively determined (82 deg) from the Wilhelmy plate data and is obtained as shown in FIG. 11 from the first time the coating is immersed in liquid water.

Stage 2. The coating is withdrawn from water. The low receding contact angle ($\theta_{rec}$) that is seen visually as the drop is withdrawn into the syringe can be calculated quantitatively from the Wilhelmy receding force distance curve (about 40 deg).

Stage 3. The coating is re-immersed in water. Remarkably, the advancing contact angle ($\theta_{adv}$) has increased to over 100°. This is easily seen visually in the picture of the drop re-impinging on the same surface already wetted by water in Stage 1. The change in the wetting behavior is quantitatively measured by the Wilhelmy advancing force distance curve (108°). Again, a coating becoming more hydrophilic when simply immersed in ambient temperature water is unprecedented. Furthermore, the change is not just a few degrees but 10's of degrees and is clearly visible.

Stage 4. When the coated slide is immersed further than the original depth, the Wilhelmy plate curve suddenly changes. Suddenly, water is impinging on a surface that has not seen liquid water. The wetting behavior changes back to hydrophilic, as seen in Stage 1. This change is easily observed visually. When the circumference of the drop re-impinging on the surface exceeds the circumference originally wetted, the contact angle of the drop changes from greater than 90 degrees (hydrophobic) to less than 90° (hydrophilic).

If the coating is dried in an oven (60° C.), hydrophilic behavior is once more seen and the contraphilic behavior is reinstated. If the coating is kept at ambient humidity and temperatures, the wetting behavior depends on humidity.

Because the change in wetting behavior is observed by testing the coating in water, the receding contact angle is always the same.

Contraphilic behavior is a completely new phenomenon. Again, surprisingly, preliminary evidence suggests that certain of the MEnOx-FOx polyurethanes are contraphilic, particularly polyurethanes modified with 2% ME7Ox-3FOx.

EXAMPLE 5

Example 5 is an extension of the "reaction on polymer" approach of Example 4 to create a biocidal surface by means of an SM. In this example, SM 36 is added to a substrate polyurethane (sometimes referred to as a "base" PU), and the surface is exposed to hypochlorite (dilute bleach) as shown in FIG. 7. The resulting coating is biocidal by virtue of the presence of the biocidal SM.

Preparation of Blends and Biocidal Coatings. Polyurethane blends containing 2-wt % dimethylhydantoin (DMH) substituted PU (36) and 98-wt % conventional polyether (PTMO) PU were prepared in tetrahydrofuran (THF). The sample films for anti-bacterial tests were prepared by simply dip-coating glass cover slips (Corning, 24×40×1.2 mm) and distributing the polyurethane evenly over both sides. The samples were placed in an upright position at ambient conditions for 24 hours and in the oven overnight at 60° C. under reduced pressure. The resulting films were transparent with no visible roughness.

Figure 13:
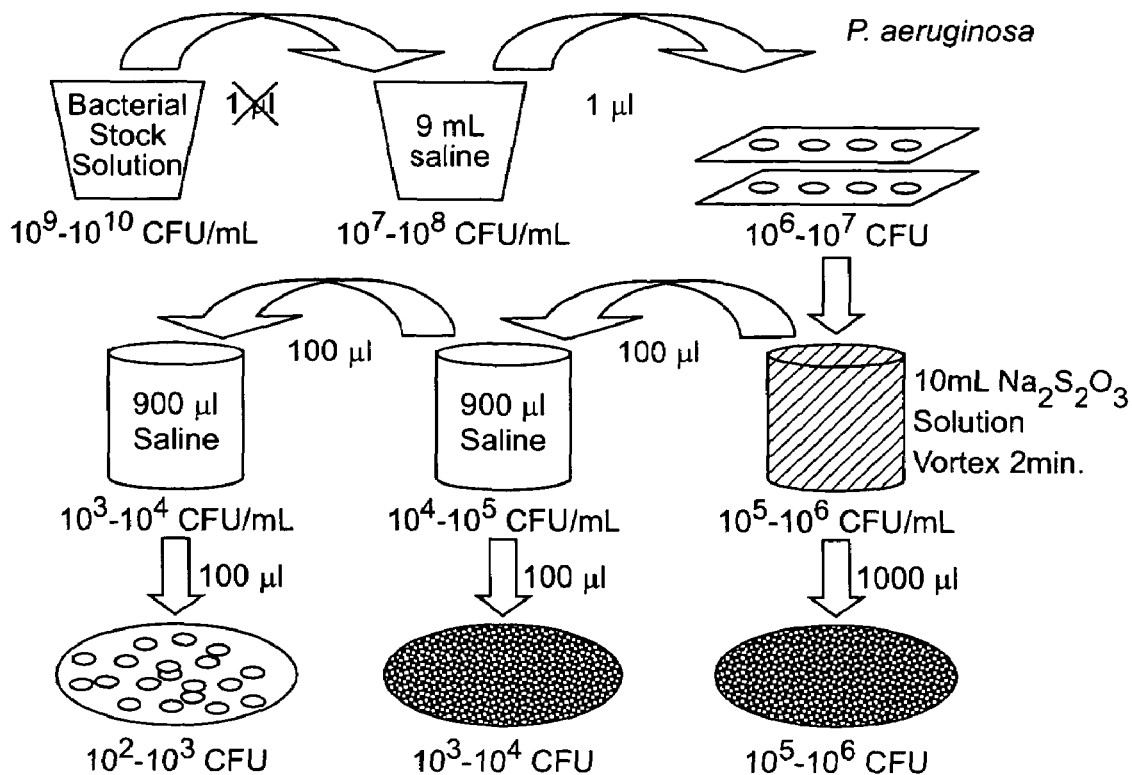
FIG. 13 shows a schematic representation of the AATCC-100 test discussed in Example 5 for demonstrating biocidal activity.

Anti-bacterial Tests: For anti-bacterial activity tests a modified version of AATCC 100 method was employed. FIG. 13 schematically shows the testing procedures. The coated cover glass slides were soaked into a solution of free chlorite (50% Clorox® solution containing 3% sodium hypochlorite) for 1 hour. Then they were rinsed with deionized (D.I.) water and placed into vacuum for overnight (60° C., 4 Torr). A known volume of inoculum containing bacteria (e.g., *E. Coli*) at a concentration of about $10^7$-$10^8$ CFU (Colony Forming Units)/ml was used for biocidal test. Slides of base PU (PTMO based PU) were used as control. The initial bacteria inoculum was diluted with saline solution (10 folds). So, this aqueous suspension contains 106-107 CFU/ml of bacteria. 1 microliter of this suspension was placed into surface of the coated glass slide. The slide was then sandwiched with an identical slide. For complete contact the "sandwich" was squeezed and a weight (beaker) was placed on the top. After different contact times (1, 1.5, and, 2 hours) the entire sandwich system was placed into aqueous sodium thiosulfate (10 ml, 0.03 wt %) solution. The resultant solution was then shaken for 5 min. An aliquot of the solution was then serially diluted (3 times) and 100 microliters of each dilution was plated on to a nutrient agar plate. Bacterial colonies on the agar plates were counted after incubation at 37° C. for 24 hours.

Figure 14:
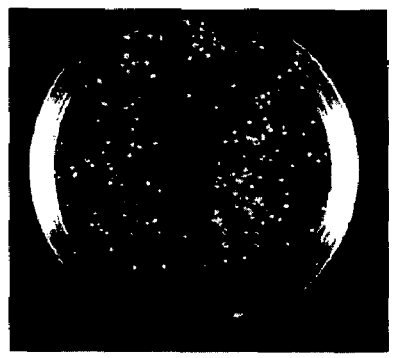
FIG. 14 shows bacterial challenge (*E. coli*) results obtained using the SMA modified bulk polymers of the present invention.
Figure 14:
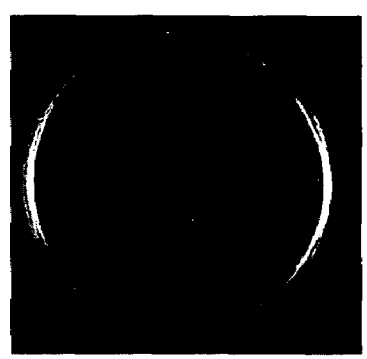

A typical test utilizing an *E. coli* challenge is shown in FIG. 14. In particular, the PU control had greater than 400 cfu's while the 98% PU, 2% biocidal SMA had 0 cfu's. All bacteria were killed in thirty minutes with a minimum of 99.9% or 3.6 log reduction.

Figure 15:
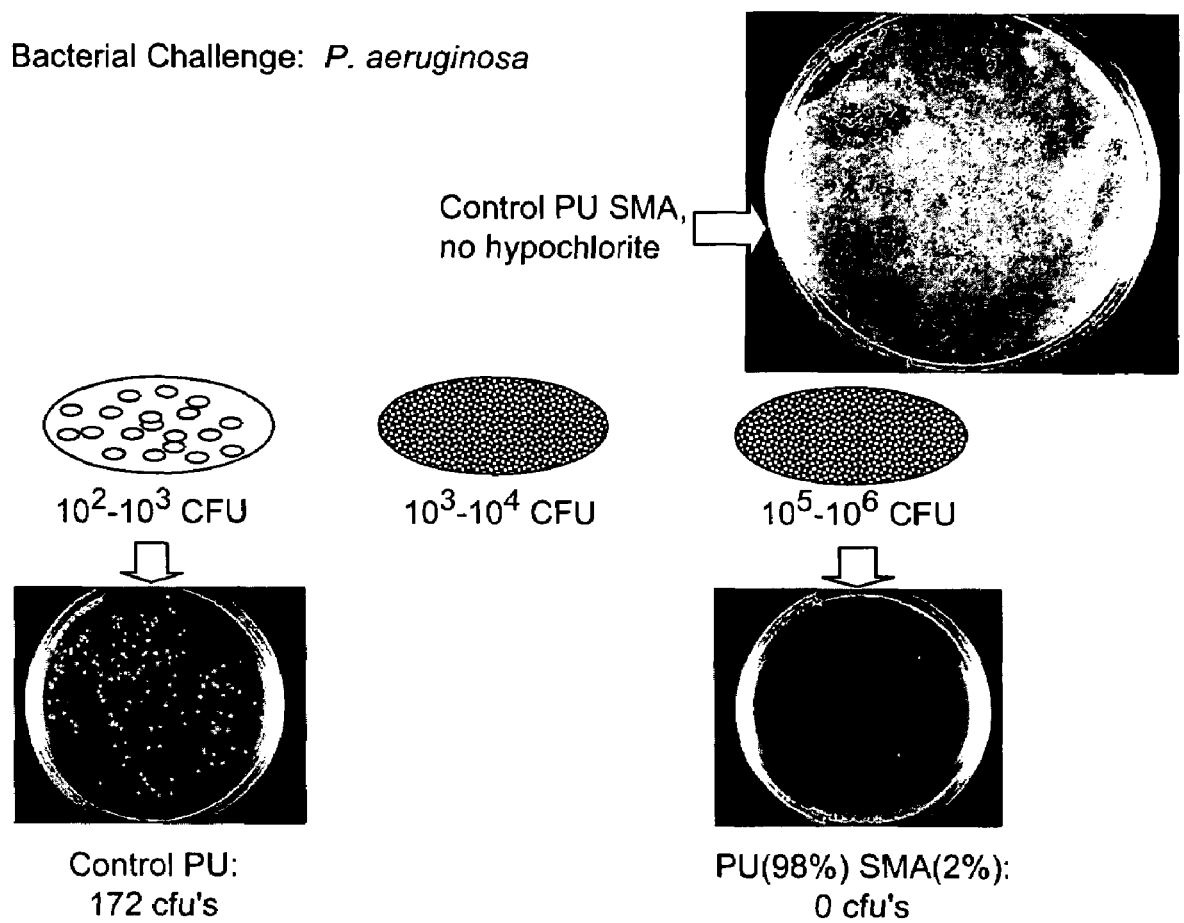
FIG. 15 shows the *P. aeruginosa* challenge results.

FIG. 15 summarizes a test challenge using a *Pseudomonas aeruginosa*. A modified AATCC-100 "sandwich" test was utilized wherein the bacterial challenge is confined between two coated surfaces as discussed above in connection with FIG. 8. To provide a more challenging challenge than the *E. coli* test, the bacterial stock solution was not diluted and a 10 times higher volume of test solution was used. With a challenge of $10^6$-$10^7$ CFUs for only 15 min, no surviving colony forming units (CFUs) were seen. In particular, the culture dish images of FIG. 10 demonstrate no surviving *P. aeruginosa* CFU's after a 30 min challenge to Gen-1 2% SMA-PU coating. The exponential growth after 24 hr development (upper right) is evident on the control pre-biocide SMA modified PU. In contrast, there are no surviving CFU's after N—Cl formation by bleach activation of the Gen-1 2% SMA-PU coating.

In a similar test, coatings were challenged against *Staphylococcus aureus*. Again, the modified AATCC-100 "sandwich" test was utilized (FIG. 8) wherein the bacterial challenge is confined between two coated surfaces. With a challenge of $10^6$-$10^7$ CFUs for only 30 min, no surviving colony forming units (CFUs) were seen.

While the SM concept was validated with a prebiocidal (Example 4) or biocidal (Example 5) moiety, 5,5-dimethylhydantoin, it will be understood by those who are skilled in the art that the functional groups surface-concentrated by the approach described above is broad. For example, the functional groups "F-3" shown in FIG. 5 may be a broad variety of hydantoin-like moieties that optimizes biocidal activity (e.g., those described in U.S. Pat. No. 6,469,177 to Worley which is incorporated by reference). Other moieties that could easily be envisaged include alkylammonium species that are known to have biocidal properties. [Tiller, J. C.; Lee, S. B.; Lewis, K.; Klibanov, A. M., Polymer surfaces derivatized with poly(vinyl-N-hexylpyridinium) kill airborne and waterborne bacteria, *Biotechnology and Bioengineering*, 2002, 79, 465471.]

Alternatively, F-3 could be a dye molecule that would protect the underlying polymer from UV degradation. F-3 could be a moiety such as —OSi(OR)$_3$ that would convert to siliceous functionalization in the presence of moisture. F-3 could be a bioactive moiety such as a peptide sequence that would favor biocompatibility. In this regard, F-3 could be the RGD peptide sequence that favors endothelialization.

The remarkable and unexpected surface properties of polymers containing soft blocks of the general structure shown in FIG. 2 demonstrates the non-obviousness of compositions employing this molecular architecture. The ability of polymers of the general structure shown in FIG. 2 is not completely understood and we are not bound by theory to explain the observed results. Nevertheless, it appears that the ability of polymers containing soft blocks of the general structure described in FIG. 2 to modify the surface behavior of a "base" polymer, even when present at low weight percent apparently stems from (a) the tendency of soft blocks to concentrate at the surface, (b) the presence of the surface-philic group, (c) the low glass transition temperature of soft block that facilitates (i) chemical modification (as in reaction on polymer shown in Example 4 or even reaction on polymer surface, as shown in Example 5) (ii) rapid surface reorganization that causes a kind of "compliance" to the medium to which the polymer is exposed (seen in high contact angle hysteresis), and facile, reversible interaction with a medium as seen in unprecedented "contraphilic" behavior discussed in Example 3, and (d) as yet little understood phenomena such as (i) described in Example 1, where the polyurethanes containing co-telechelics have higher $\theta_{adv}$ and lower $\theta_{rec}$ than the parent homo-telechelic PUs and (ii) where a new synthetic procedure in Example 2 led to the discovery of amplification of hydrophobicity, which occurred when the cotelechelic had a block structure of fluoro-groups (F1) rather than a random structure of F1 groups.

While the invention has been described in terms of its preferred embodiments, those skilled in the art will recognize that the invention can be practiced with modification within the spirit and scope of the appended claims.

The invention claimed is:

1. A polymeric article or coating, comprising:
   a bulk polymer phase; and
   a surface active polymer or macromonomer that contains a hard block and a soft block wherein said soft block has two or more types of repeat units which are different from each other, wherein at least one of said two or more types of repeat units favors migration to a surface of said bulk polymer phase and is concentrated primarily on said surface;
   wherein said at least one of said two or more types of repeat units is selected from the group consisting of —(CH$_2$)n(CH$_2$)mF or —(CH$_2$)n(CF$_2$)mH where n ranges from 1 to 10 and m ranges from 1 to 12; and wherein at least a second repeat unit of said two or more repeat units includes a hydantoin like moiety.

2. The polymeric article or coating of claim 1 wherein at least one of said two or more types of repeat units provides biocidal or prebiocidal activity.

3. The polymeric article or coating of claim 1 wherein at least one of said two or more types of repeat units provides surface wettability altering activity.

4. The polymeric article or coating of claim 1 wherein at least one of said two or more types of repeat units provides an indicator.

5. The polymeric article or coating of claim 4 wherein said indicator is selected from the group consisting of color change, fluorescence, phosphorescence, and chemiluminescence.

6. The polymeric article or coating of claim 1 wherein at least one of said two or more types of repeat units provides a modifiable leaving group.

7. The polymeric article or coating of claim 1 wherein said surface active polymer and said bulk polymer phase are both polyurethanes.

8. The polymeric article or coating of claim 1 wherein at least a second repeat unit of said two or more types of repeat units is biocidal or prebiocidal.

9. The polymeric article or coating of claim 1 wherein said surface active polymer or macromonomer comprises less than 10 percent by weight of said polymeric article or coating.

10. The polymeric article or coating of claim 9 wherein said surface active polymer or macromonomer comprise about 0.1-3 percent by weight of said polymeric article or coating.

11. The polymeric article or coating of claim 1 wherein at least some of the monomeric units in said bulk polymer phase and said surface active polymer or macromonomer are the same.

12. The polymeric article or coating of claim 1 wherein at least a second repeat unit of said two or more repeat units includes a dye.

13. The polymeric article or coating of claim 1 wherein at least a second repeat unit of said two or more repeat units includes a moiety that converts to siliceous functionalization in the presence of moisture.

14. The polymeric article of claim 13 wherein said moiety is —OSi(OR)$_3$.

15. The polymeric article of claim 1 wherein said soft block comprises three repeat units each of which are different from each other.

16. The polymeric article of claim 1 wherein at least a second repeat unit of said two or more repeat units includes a bioactive moiety.

17. The polymeric article or coating of claim 1, the bulk polymer phase having bulk properties; and the surface having a property of interest and the bulk properties of the bulk polymer phase being unaffected.

* * * * *